United States Patent
McLoughlin et al.

(10) Patent No.: US 12,390,399 B2
(45) Date of Patent: Aug. 19, 2025

(54) MEDICATION ERROR DETECTION SYSTEM

(71) Applicant: Bristol-Myers Squibb Company, Princeton, NJ (US)

(72) Inventors: Martin John McLoughlin, Hillsborough, NJ (US); Stephen Lawrence Zieminski, East Brunswick, NJ (US); Jeffrey Manfred Gunnarsson, Baltimore, MD (US); Nitin Venkat Vudathala, Baltimore, MD (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 537 days.

(21) Appl. No.: 17/770,816

(22) PCT Filed: Oct. 27, 2020

(86) PCT No.: PCT/US2020/057472
§ 371 (c)(1),
(2) Date: Apr. 21, 2022

(87) PCT Pub. No.: WO2021/091723
PCT Pub. Date: May 14, 2021

(65) Prior Publication Data
US 2022/0370291 A1   Nov. 24, 2022

Related U.S. Application Data

(60) Provisional application No. 62/932,814, filed on Nov. 8, 2019.

(51) Int. Cl.
*A61J 1/20* (2006.01)
*G06F 12/06* (2006.01)
*G16H 20/17* (2018.01)

(52) U.S. Cl.
CPC .......... *A61J 1/2089* (2013.01); *A61J 1/2048* (2015.05); *G06F 12/0653* (2013.01);
(Continued)

(58) Field of Classification Search
CPC .. A61J 1/10; A61J 1/065; A61J 1/2003; A61J 1/2048; A61J 1/2089; A61J 1/2096;
(Continued)

(56) References Cited

U.S. PATENT DOCUMENTS 4,629,164 A   12/1986  Sommerville
4,756,706 A   7/1988   Kerns et al.
(Continued)

FOREIGN PATENT DOCUMENTS

CH   576251 A5    6/1976
CN   101360484 A  2/2009
(Continued)

OTHER PUBLICATIONS

Office Action from Chinese Application No. 202080093649.6 dated Aug. 16, 2023.
(Continued)

*Primary Examiner* — Adam Marcetich
*Assistant Examiner* — Timothy L Flynn
(74) *Attorney, Agent, or Firm* — Budzyn IP Law, LLC

(57) ABSTRACT

Various embodiments are provided herein for checking proper inclusion and sequencing of drug modules in a combinatorial drug delivery device.

8 Claims, 29 Drawing Sheets

(52) U.S. Cl.
CPC ....... *G06F 12/0676* (2013.01); *A61J 2205/60* (2013.01); *A61M 2205/6018* (2013.01); *A61M 2205/6027* (2013.01); *G16H 20/17* (2018.01)

(58) Field of Classification Search
CPC .............. A61J 2205/60; A61J 2200/70; A61M 2205/6018; A61M 2205/3569; A61M 2205/50; A61M 2205/6036; A61M 2205/6009; A61M 2005/14208; A61M 5/1413; A61M 5/16827; A61M 5/1409; A61M 5/142; G06F 12/0653; G06F 12/0676; G16H 20/17; G16H 40/63; G16H 40/67

See application file for complete search history.

(56) References Cited

U.S. PATENT DOCUMENTS

| | | | |
|---|---|---|---|
| 7,771,334 | B2 | 8/2010 | Bailey et al. |
| 2004/0171985 | A1* | 9/2004 | Schubert ............. A61M 5/1413 604/93.01 |
| 2008/0015493 | A1 | 1/2008 | Childers et al. |
| 2011/0021978 | A1 | 1/2011 | Martin et al. |
| 2012/0179130 | A1 | 7/2012 | Barnes et al. |
| 2013/0336814 | A1 | 12/2013 | Kamen et al. |
| 2016/0051750 | A1* | 2/2016 | Tsoukalis ............ A61M 5/1689 235/375 |
| 2017/0128669 | A1 | 5/2017 | Barnes et al. |
| 2019/0091406 | A1 | 3/2019 | Okamura et al. |

FOREIGN PATENT DOCUMENTS

| | | |
|---|---|---|
| CN | 101394878 A | 3/2009 |
| CN | 103998075 A | 8/2014 |
| EP | 0960627 A2 | 12/1999 |
| EP | 2930710 A1 | 10/2015 |
| GB | 2141997 B | 5/1986 |
| WO | 1993010851 A1 | 6/1993 |
| WO | 2012080481 A1 | 6/2012 |
| WO | 2013043889 A1 | 3/2013 |
| WO | 2013102496 A1 | 7/2013 |
| WO | 2019217820 A1 | 11/2019 |
| WO | 2019217845 A1 | 11/2019 |
| WO | 2019217864 A1 | 11/2019 |

OTHER PUBLICATIONS

International Search Report and Written Opinion of the International Searching Authority from PCT International Application No. PCT/US2020/057472, dated May 26, 2021.

* cited by examiner

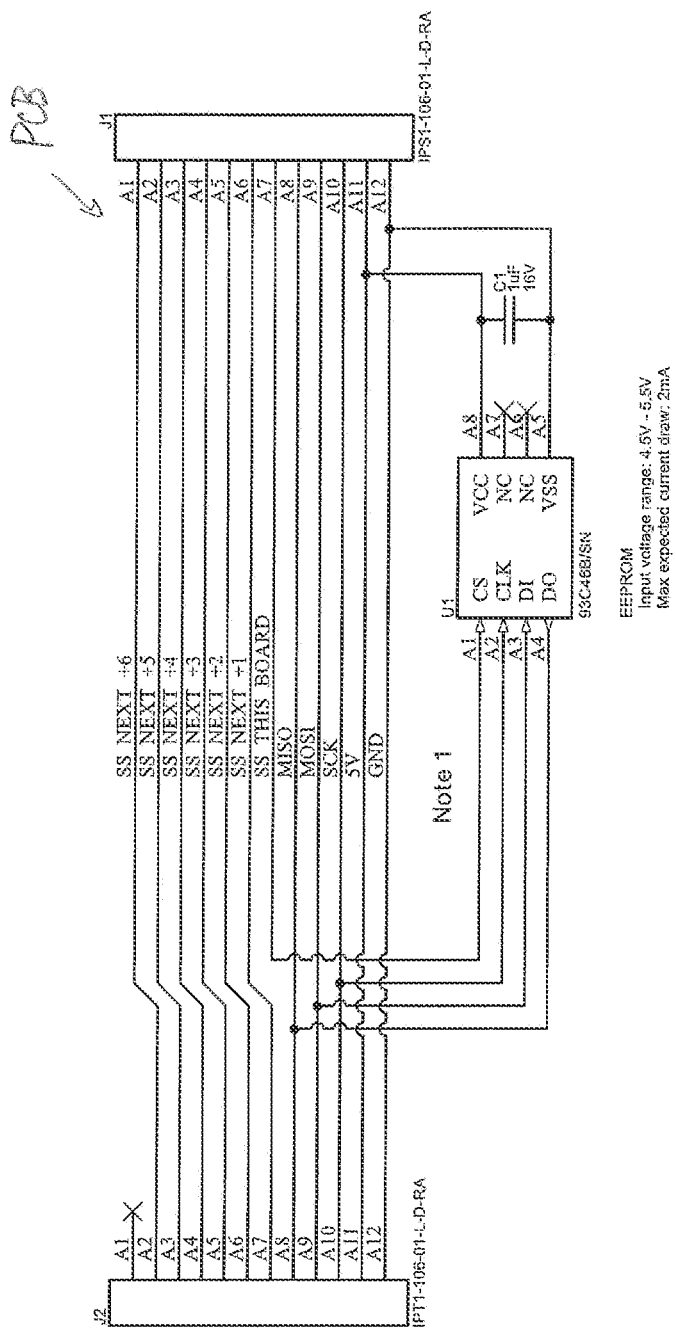
FIG. 26

MEDICATION ERROR DETECTION SYSTEM

CROSS-REFERENCE TO RELATED APPLICATIONS

This application is a National Stage Application under 35 U.S.C. § 371 of PCT Application No. PCT/US2020/057472, filed Oct. 27, 2020, which claims the priority benefit of U.S. Provisional Application No. 62/932,814, filed Nov. 8, 2019; the contents of which are herein incorporated by reference in their entireties.

BACKGROUND OF THE INVENTION

Drug combinatorial systems are shown and described in: U.S. Provisional Patent Appl. No. 62/670,266, filed on May 11, 2018; PCT Appl. No. PCT/US2019/031727, filed May 10, 2019; PCT Appl. No. PCT/US2019/031762, filed May 10, 2019; and, PCT Appl. No. PCT/US2019/031791, filed May 10, 2019. All of the aforementioned patent applications are by the same assignee as herein. As shown in the aforementioned patent applications, drug modules of different liquid drugs may be provided in various combinations to provide different (individualized) drug combinations. The drug modules may be nested, i.e., connected, in series or in parallel, on a tray or other base structure. Alternatively, the drug modules may be serially connected (vertically and/or horizontally) directly to one another. U.S. Provisional Patent Appl. No. 62/670,266, PCT Appl. No. PCT/US2019/031727, PCT Appl. No. PCT/US2019/031762, and, PCT Appl. No. PCT/US2019/031791, are incorporated by reference herein in their respective entireties.

A serially-connected combinatorial system, such as that illustrated schematically in FIG. 1 for IV fusion, has the advantage in comparison with the nested designs illustrated in FIGS. 2 and 3 in that it does not require a separate tray component to make the fluid connections and is therefore more efficient in components and supply chain.

In the nested system, the tray design can 'store' information on the correct configuration of the modules through the inherent design and layout of the tray design. For example, the tray may provide a configuration (e.g., mechanical cooperating features, such as "lock and key" features) that guarantee only the correct drug modules can be inserted into the nests of the tray and that the correct drug modules are arranged in the correct order. This acts as a safety check in preparing the drug modules for use. In contrast, the serially-connected system does not have a tray-type element and, thus, lacks the ability to have a safety check on this basis.

A desirable feature of the modules in both the serially-connected and nested systems is that they should be universal in design to the greatest extent possible so that a minimal number of component parts is required to use them as a system. A limitation of the nested systems is that their use of mechanical features to identify all of the possible drugs and strengths that may be used, requires different components for different arrangements to be molded and held in stock. This creates logistical complexity in the supply chain and requires manufacture of multiple mold tools for each arrangement (e.g., each "lock and key" arrangement). With a portfolio of many drugs at different strengths intended for use in combination with each other, the number of molded components that must be manufactured and stocked may grow excessively large.

Because the serially-connected designs do not have a configuration tray, and, because all modules must fit to each other, they must be mechanically universal by design. This universality of design means that, unlike with the nested designs, it is possible for modules to be assembled in an incorrect order.

Because tray-based mechanical means of error prevention are not possible in the serially-connected case, it is desirable to implement other means of detecting configuration errors in the serially-connected system and hence prevent the occurrence of medication errors.

BRIEF DESCRIPTION OF THE DRAWINGS

FIG. 26 shows a substrate (e.g., PCB) arrangement for the lane-shifting electronic connections.

DETAILED DESCRIPTION OF THE INVENTION

Figure 1:
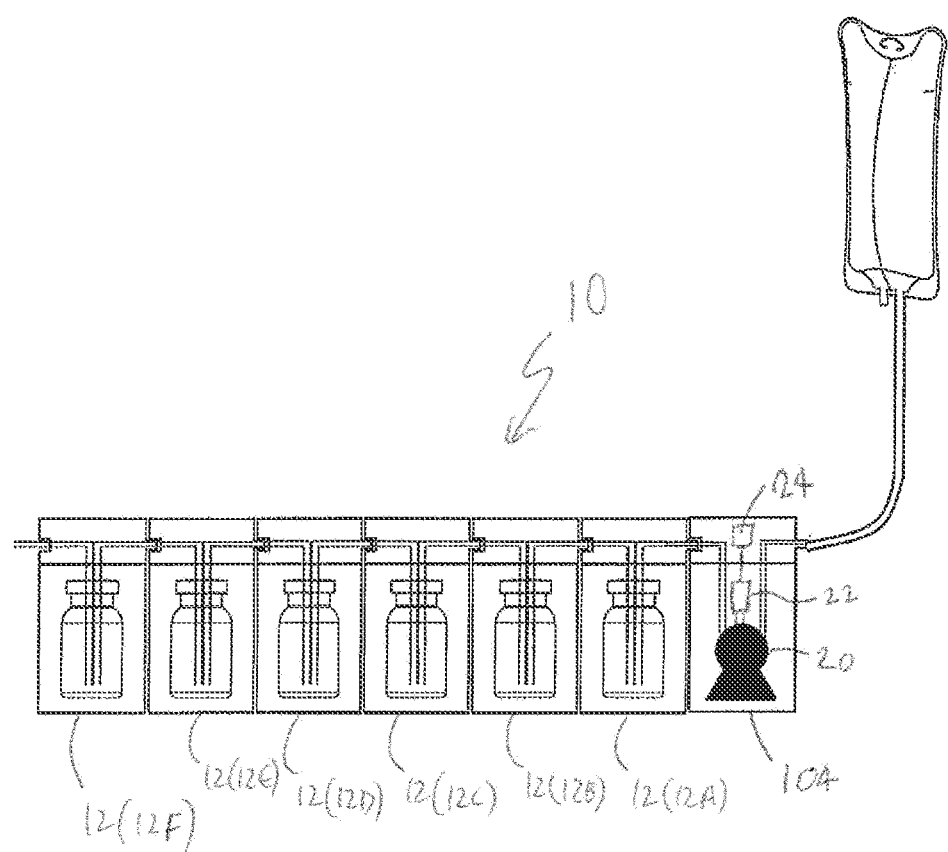
FIG. 1 is a schematic illustration of the serially-connected module based, IV combinatorial transfer system with pump housing and infusion bag shown.

According to the present invention, an arrangement for a serially-connected system can be realized for checking the accuracy of the assembled modules by understanding that information about the correct configuration is required from two distinct levels within the system. The first level is that of individual modules. Modules must store information about their contents and provide access to that information.

The second level from which information about correct configuration is required is the system configuration level. That is, information about the sequence of the individual modules assembled in the entire system.

Confirming the system level configuration requires that the type (identity) and state of each module at each location in the assembly are identified.

Information about the module type can be encoded or programmed into the individual module at the factory during manufacturing. However, due to the requirement for universality of the module design, the modules are preferably manufactured the same. It is only when a system is being prescribed for use that system configuration information (that is the type and order of modules in the assembly) is defined (i.e., the actual drugs and sequence of modules are determined). This information is recorded to be available for interrogation during assembly and use in the field (i.e., when the drugs to be used are actually determined).

As will be recognized by those skilled in the art, a serially-connected system is useable with a vast number of drugs and drug concentrations. As a result, the number of permutations with the system may be in the millions, if not greater. For example, consider a portfolio of ten drugs, each available at three different strengths for a total of thirty distinct drug containers which are to be combined together in combination therapies using a serially-connected system. Additionally, there may be a diluent module that can be combined with any of the drug modules in any order. The type of each of the thirty-one containers must be identifiable whilst maintaining universality of the design of the modules.

To illustrate a possible example, assuming that the number of modules in a serially-connected system is limited to six but their order of assembly is otherwise unconstrained, and, assuming that the most different drugs that can be combined together is three (that is single, doublet and triplet combinations are permitted), then for each triplet combination of drugs, there are 1,092 possible configurations of the modules in the assembly, giving 1,092 possible drug module configurations. Now assume that for each particular drug, different strengths are available so that there are three choices of strength for each module in a serially-connected system. In this case, the number of unique configurations of the modules that can be achieved is 597,870. The number of configurations grows rapidly with the inclusion of varying strengths.

Without controls, the risk of a medication error being made is proportional to the number of possible ways in which a system can be configured. If the total number of possible configurations is $C_T$ then the probability of an assembly of modules chosen at random giving the correct configuration is $1/C_T$. This can be used to define the probability of medication error as $1-1/C_T$. In the first example above with 1,092 possible combinations, the probability of error is 0.9991. In the second example above with 597,870 possible combinations, the probability of error is 0.999998. Therefore, a high probability of error exists with the use thereof.

Applicant has realized that module level type information for a serially-connected system can be encoded as binary code by the use of settable switches, possibly, at the time of assembly. Enough switches are required to provide sufficient switch states to encode for all of the drug types and concentrations. In the aforementioned case often drugs at three strengths plus one diluent module and a possible 'empty' or 'vacant' state, thirty-two switch states may be utilized (i.e., switch state for each drug at a designated concentration (30 switch states), one switch state for a diluent, and one switch state for an empty, by-pass module). Thirty-two switch states can be achieved by the use of five switches connected in parallel (the person skilled in the art will know that this is commonly known as a '5-gang' switch). If an open switch represents binary '0' and a closed switch represents binary 1 then the status of each switch in the gang for a module represents one bit in a five-bit binary number. The number of possible binary states in an n-switch parallel array is given by $2^n$. In this case n=5 and therefore the number of possible switch states is $2^5=32$ which is sufficient for the range of modules. For example, the module for drug 3, strength 1 may be encoded by the five-bit binary number 00110 (decimal six). The switch state for this module is shown schematically in FIG. 4.

In order to maintain simplicity of design and keep the module size to a minimum, the actual switches need not be switches in the conventional sense. Instead, they may simply be a plurality of electrical conductors, e.g., five electrical conductors, connected in parallel with each other on a module. Setting of the switches to encode for a particular module type is achieved by severing or otherwise breaking the desired conductors to disrupt conductive paths so that they are 'switched off'. For example, to set the switches in the example of FIG. 4, $1^{st}$, $4^{th}$ and $5^{th}$ conductors would be cut, leaving the $2^{nd}$ and $3^{rd}$ wires intact to encode the binary number 00110 (the $1^{st}$, $4^{th}$, and $5^{th}$ conductors being "off", considered "0" in binary, with the $2^{nd}$ and $3^{rd}$ conductors being intact and "on", considered "1" in binary). The electrical conductors are preferably frangible with the breaking of the conductors being achievable by any means, including, but not limited to, mechanically, electrically, e.g., by fusing the desired wires with an applied current, and/or by other suitable means that can be automated and integrated into a high speed assembly operation, e.g., laser beam. The irreversibility of such switch setting is desirable in this case because once set correctly, e.g., at the factory, the switch states should not be changed.

To minimize tampering, it is preferred that the electrical conductors be formed in the modules to not be readily accessible with the module being in the stream of commerce. It is preferred that the conductors be covered, particularly once encoded (conductors being broken as needed). For example, the conductors may be over-molded or covered by a lid or other covering that is secured to the module, preferably, to resist removal (e.g., being fused, adhered, etc.).

It is possible to allow for the breaking of electrical conductors post-manufacturing, e.g., at a location, such as a pharmacy, where drug is loaded into the modules. For example, non-conductive, press-down spikes or the like may be formed in the module aligned with the electrical conductors. Deflection of the spikes, inwardly in the body of the module, will cause breakage of the corresponding electrical conductors. With the spikes being non-conductive (e.g., thermoplastic), electrical flow through the respective conductors is disrupted. To limit inadvertent displacement of the spikes, the spikes may be over-molded or otherwise provided with a restraint which must be removed to allow for deflection. With over-molding, a threshold force may be targeted needed to overcome the inherent rigidity of the over-mold, which must be exceeded to allow for deflection of the spikes. In addition, or alternatively, a panel or other covering may be provided which covers, and spans, all of the spikes, blocking access thereto. Removal of the panel is required to access the spikes. Once the target spikes have been deflected for encoding the corresponding drug's designation, the panel is re-secured to the module. Re-securement may be arranged to resist further removal of the panel, for example, by providing detents or other features which snap into a locked position with re-securement of the panel.

The module may be loaded with the target drug before and/or after encoding the module with the drug type number in binary form. This may happen at the manufacturing stage or later, including at point of use. As shown in FIG. 1, with all modules 12 intended for a system 10 having been prepared (encoded and loaded), the modules 12 may be serially connected to one another and to a controller housing 104 to form the system or assembly 10. The system 10, including any aspect thereof, may be formed in accordance with any of the embodiments disclosed in any of U.S. Provisional Patent Appl. No. 62/670,266, PCT Appl. No. PCT/US2019/031727, PCT Appl. No. PCT/US2019/031762, and, PCT Appl. No. PCT/US2019/031791. For illustrative purposes, exemplary features of the system 10 are described herein. As will be recognized by those skilled in the art, the subject invention is useable with any of the combinatorial drug delivery devices, including being useable with any of the elements thereof (e.g., modules 12, manner of connecting modules 12, controller housing 104, etc.), disclosed in any of the aforementioned patent filings.

Figure 2:
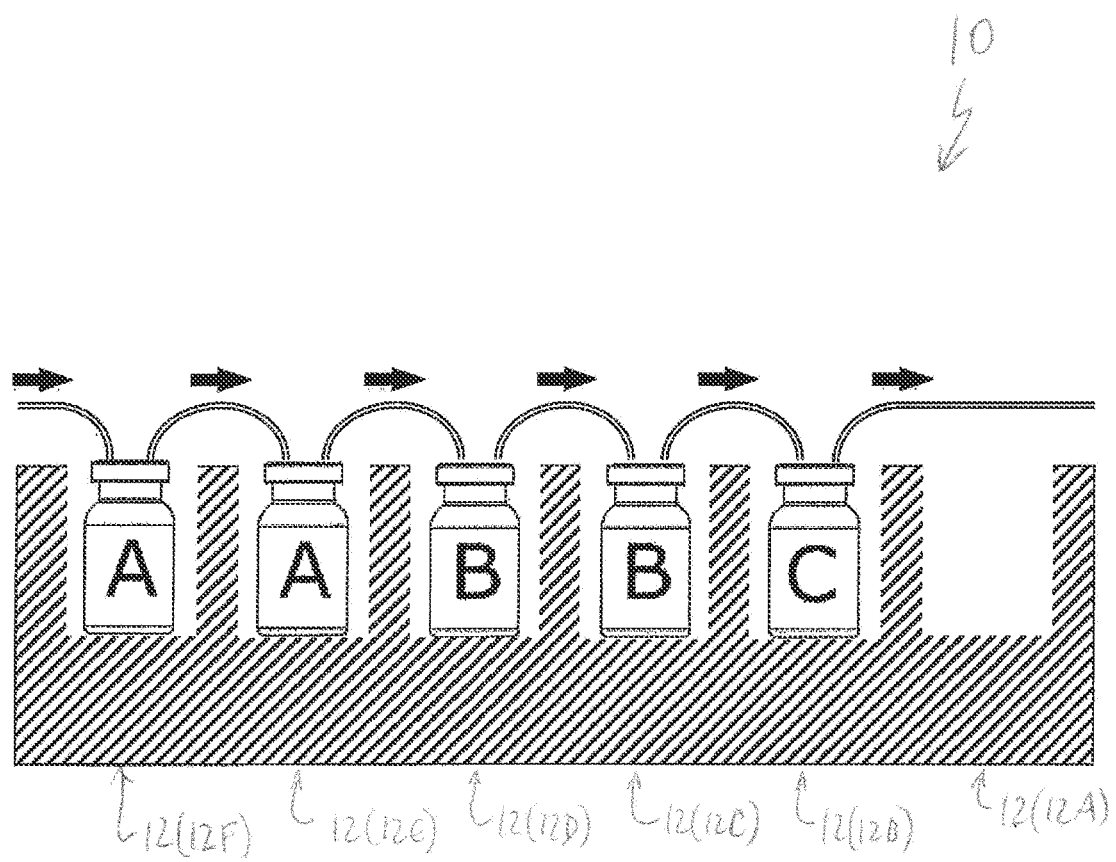
FIG. 2 is a schematic illustration of the nested tray IV combinatorial transfer system.

As shown in FIG. 1, the modules 12 (12A-12F) may be serially connected to define a single flow path which extends from the reservoir of the ultimate module and passes through the reservoir of each successive module to the controller housing 104. The flow path need not be continuous, for example, having lengths (e.g., tubing) which extends between adjacent reservoirs. As shown in FIG. 2, the flow path may be arranged so that the outlet of one module is in communication with an inlet of an adjacent module, such that the drug of the first-mentioned module must pass through the second-mentioned module, and so forth, in advancing along the fluid path towards the controller housing 104. The fluid path may traverse one or more reservoirs of the serially-connected modules 12. One or more of the modules 12 may be by-passed, with no liquid drug, such as module 12A in FIG. 2. The outlet of the flow path from the first module, e.g., module 12A, is in communication with an inlet channel of controller housing 104, as shown in FIG. 1 (the first module, e.g., module 12A, being closest to the controller housing with the furthest, or last, module, e.g., module 12F, being considered the ultimate module). It is preferred that a singular flow path be utilized, but it is possible to have multiple fluid paths (e.g., more than one series of serially-connected modules is provided in parallel, connected by a manifold or common outlet). To best facilitate evacuation of the reservoirs, the flow path may be vented in the ultimate module, e.g, at the terminus of the flow path.

In a preferred embodiment, the controller housing 104 contains a pump 20 having an inlet in communication with the inlet channel. The pump 20 is preferably driven by an electrical motor 22, which is controlled by a computing processing unit (CPU) 24 located in the controller housing 104. The pump 20 is sized to provide sufficient negative pressure (i.e., suction) to evacuate all of the reservoirs of the serially-connected modules 12. Various pumps may be utilized, such as a positive displacement pump, which is capable of drawing drug through the flow path. An outlet channel is provided for the controller housing 104 to be in communication with the discharge of the pump 20. The outlet channel being accessible externally of the controller housing 104 to allow connection with further tubing or other implements to direct flow of the discharged drug. The discharged drug may be directed to a collection vessel, such as an IV bag, or to a drug delivery device, such as a delivery needle inserted in a patient (e.g., butterfly needle).

Figure 3:
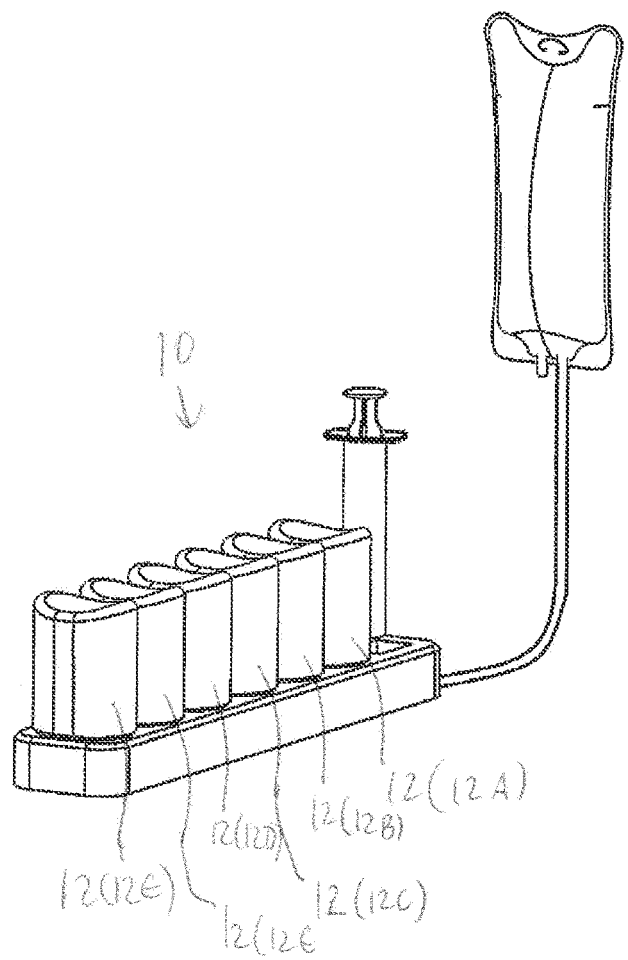
FIG. 3 is a schematic illustration of the nested tray IV combinatorial transfer system with integral syringe pump and infusion bag shown.

In an alternative, no pump is provided with the controller housing 104. An external pump may be utilized to draw fluid through the flow path, e.g., as shown in FIG. 3 (a hand operated syringe pump). With no pump in the controller housing 104, it is preferred that a valve be located in-line between the inlet and outlet channels inside the controller housing 104. It is preferred that the valve be controlled by an electronic actuator that, in turn, is controlled by the CPU 24. The CPU 24 is configured to cause the actuator to selectively open and close, thereby selectively allowing flow of drug through the outlet channel. The inlet channel may be connected to an inlet of the valve, and the outlet channel may be connected to an outlet of the valve.

The valve may be provided in combination with the pump 20 contained in the controller housing 104. The valve may be controlled by the CPU 24, as discussed above. One or more check valves may be also used along the flow path (e.g., in the modules 12) and/or within the controller housing 104, limiting flow through the flow path to one direction.

Figure 4:
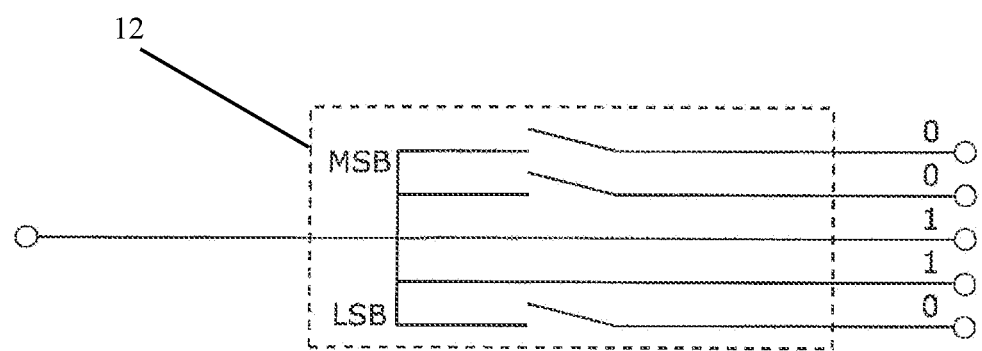
FIG. 4 is a schematic illustration of a five-gang plug integrated into the module to encode the module type.

It Is preferred that the CPU 24 have an associated memory in which may be stored an authentication code. The authentication code can be put into memory when the modules 12 are encoded. In this way, a kit of the encoded modules 12 and controller housing 104 are put together for shipping and later assembly. The system, as described below, allows for generation of a code, based on the encoding of the individual modules and the sequence of the modules. By way of non-limiting example, FIG. 4 shows a configurable switch gang, e.g., with five switchable electrical conductors, which may be provided on each of the modules 12. The generated code is compared against the authentication code for comparison. With a match, there is indication that the correct modules and correct sequence of modules are in place. This causes the CPU 24 to actuate any valves to an open position and/or place the pump 20 into an active state, whereby, the pump 20 is actuated or is actuatable by a user-operated switch. It is also possible to provide the system with a transmitter/receiver to transmit the generated code to a remote server, mobile device, etc., where the comparison with the authentication code takes place. An electronic message is returned either allowing or denying drug dispensing. With this arrangement, the controller housing is not customized to the particular system (i.e., the authentication code based on the actual drug modules and sequence thereof does not need to be stored in the device). In addition, the receiver may be utilized to receive the authentication code from an external source (remote server, mobile device, etc.), also eliminating the need to pre-store the authentication code on the CPU 24.

Figure 5:
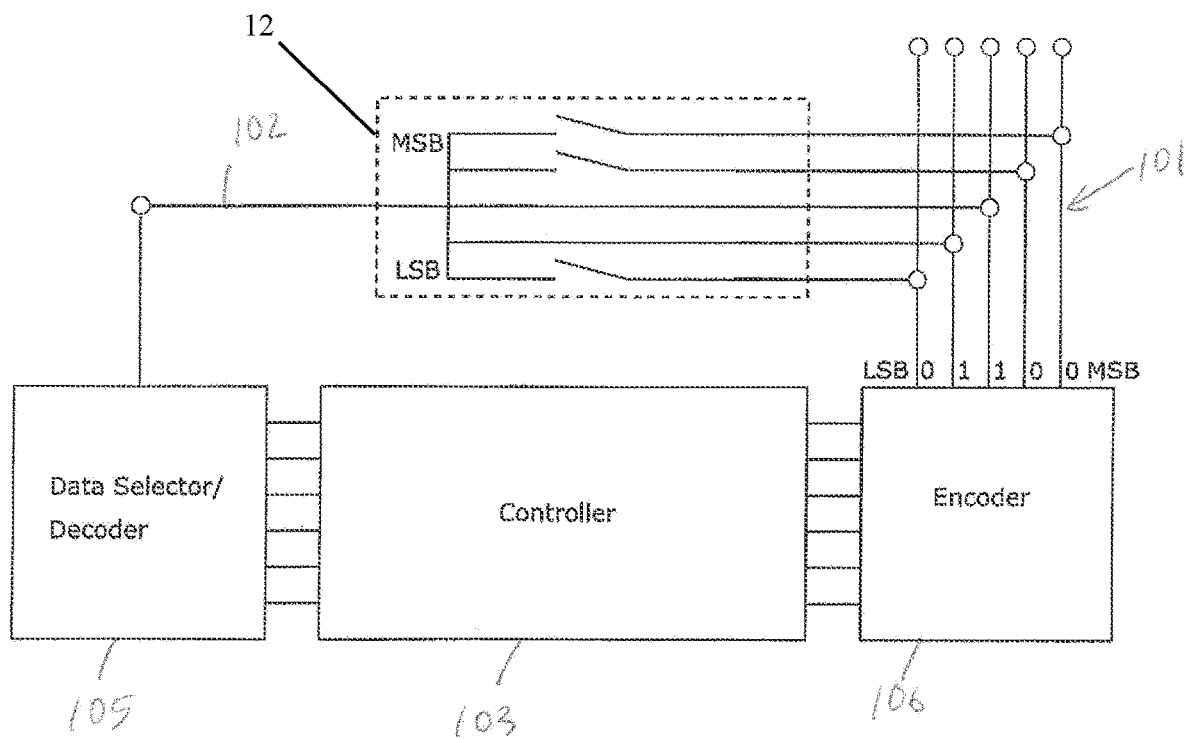
FIG. 5 is a schematic illustration of a circuit that can be used to interrogate the encoding of the module from FIG. 4.

The code may be generated by the system using the circuit shown in FIG. 5. The wires which form the switch gang in the modules 12 are connected to the data transmission lines of the data bus 101. The data bus 101 has one transmission line for each switch in the gang, in this case five, forming a five-bit data bus. In the case of the binary six numbered module type described previously, the binary number 00110 appears in parallel at the input pins of the encoder integrated circuit. By means of standard digital electronic components including but not limited to decoders, encoders, multiplexers, de-multiplexers, logic gates, read-only memories, programmable logic arrays, microprocessors and displays the binary number read from the module array may be used to display more information about the module. For example, a programmable logic array or read-only memory may be used as a look-up table to store further information about the module corresponding to 00110 such as drug identity and strength.

However, interrogating individual modules does not provide information about the system level configuration when the modules are assembled together, i.e., the sequence of the assembled modules. To achieve this, a means of uniquely addressing each module in the assembly is required.

Figure 6:
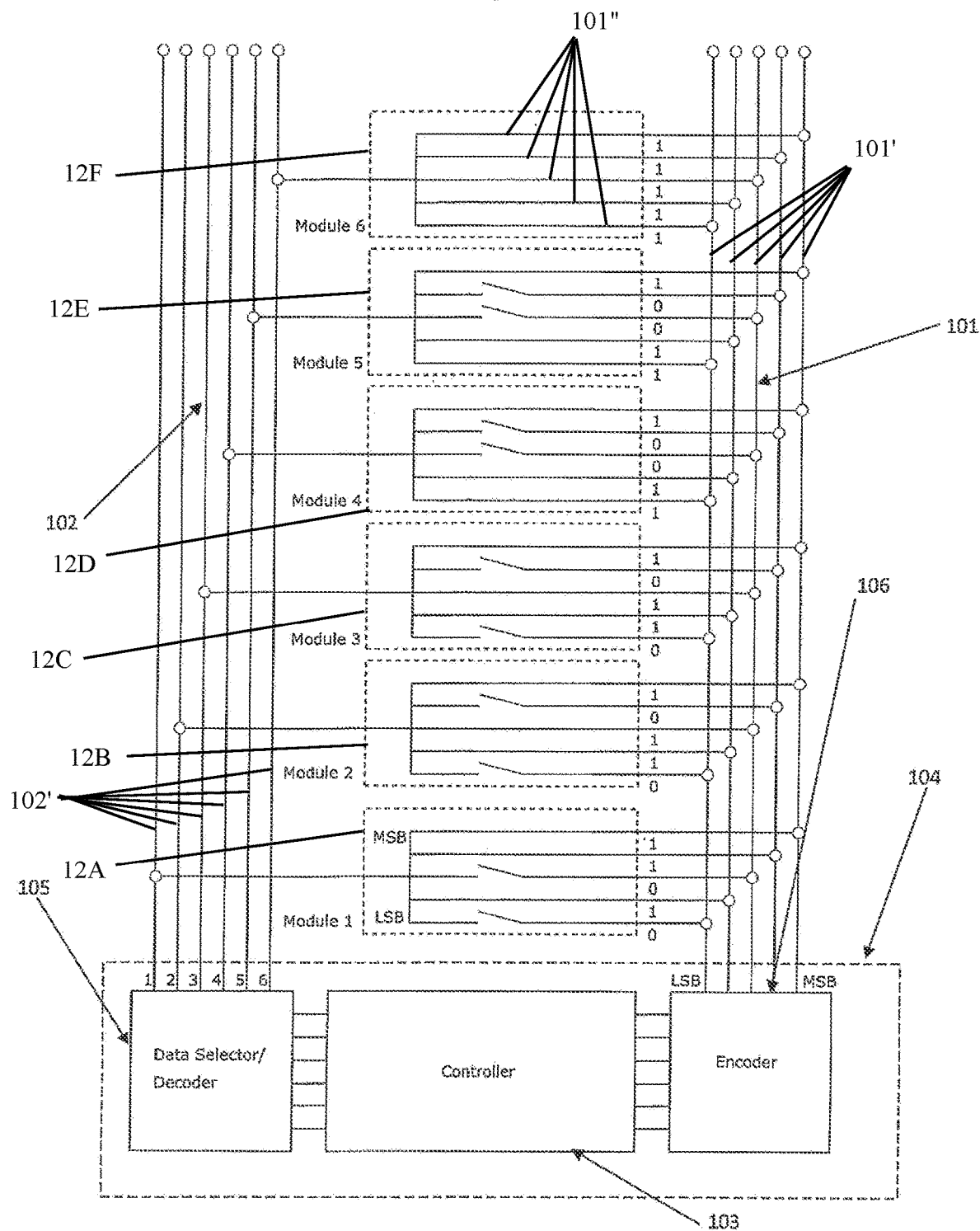
FIG. 6 is a schematic illustration of a circuit that can be used to interrogate the status of all of the modules in an assembly.

Addressing of the modules in sequence, i.e., as an assembly, may be achieved by the circuit shown schematically in FIG. 6.

The modules 12 of the assembly 10 are connected in parallel with the data bus, 101, and an address bus, 102. In general, the address bus has N transmission lines where N is equal to the maximum number of modules permissible in an assembly so that there is one transmission line for each module in the assembly, in this case six. Various quantities may be utilized.

The data and address buses 101, 102 are connected to an electronic controller, 103, integrated into the controller housing, 104, via a data selector/decoder integrated circuit, 105, and an encoder integrated circuit, 106, respectively. By means of the controller, 103, the data selector/decoder, 105, can address and supply electronic current to each conductor, on each of the modules, in sequence. By means of the controller, 103, synchronization of the addressing sequence of the decoder, 105, with module type binary number read at the output lines of the data bus, 101, enables the identity of each module 12 (12A, 12B, 12C, 12D, 12E, 12F, . . . ) in the assembly 10 to be read in sequence. Hence, system level type and configuration data can be established as is required to confirm the correct identity of modules and their configuration in the assembly. The switch line for the least significant bit is labelled, LSB, and, that for the most significant bit is labelled MSB. The identity of modules in the assembly shown in FIG. 6 is listed in Table 1 below.

TABLE 1

| Module Number | Binary ID | Decimal ID |
|---|---|---|
| 12A | 11010 | 26 |
| 12B | 10110 | 22 |
| 12C | 10110 | 22 |
| 12D | 10011 | 19 |
| 12E | 10011 | 19 |
| 12F | 11111 | 31 |

It will be understood by the person skilled in the art that the functionality required of the controller, 103, may be constructed from standard electronic components and integrated circuits which may include but are not limited to memory elements (RAM, ROM), microprocessors, timers/clocks, logic gates, multiplexers, de-multiplexers, programmable logic arrays, shift registers and so on.

In embodiments, the digital electronic circuits of the controller, 103, can be programmed to store the particular configuration (e.g., pre-stored or stored in response to receipt by the receiver of the controller 103) required for a particular prescription and can automatically make a logical comparison between the expected binary code for each module 12 with that read at the output from the data bus 101. In embodiments, this expected configuration may be programmed into memory elements by any suitable input means such as by keypad entry, optically using e.g. bar or quick response (QR) codes or by radio frequency means e.g. radio-frequency identification (RFID), near field communication (NFC) or personal area network (PAN) technology e.g. using the Bluetooth, Zigbee, Ant or other personal area networking protocols. Alternatively, the determined binary code may be transmitted to a remote server, or the like, where the expected binary code is stored for a comparison to be made. With a determined match, an activation code may be transmitted to the assembly to signify correctness of the assembly. An expected activation code may be stored in the controller 103 to allow for comparison.

In embodiments, it may be advantageous to concatenate the binary numbers received at the output from each module into a single binary number. For example, the 6×5 bit binary numbers of the previous example can be concatenated into a single 30 bit binary number. For example, if concatenating from the last module 12F to the first module 12A in the example of FIG. 6, the resulting number is 111111001110011101101011011010. Likewise, the number may be concatenated in a direction from the first module 12A to the last module 12F with a resulting number of 110101011010110100111001111111.

The verification of the correct configuration of the correct modules then amounts to the comparison of this 30 bit binary number with the 30 bit binary number expected for the prescription configuration. The binary number $2^{30}=32^6=1,073,741,824$ and represents the total number of ways in which 32 objects can be arranged in a assembly of 6 and so is the number of states that can be encoded in this example (note that a large number of these states are duplicates and so the actual number of unique states is substantially less than this).

The verification of the correct configuration acts as a key for the CPU 24 to actuate the pump 22 and/or valve. The CPU 24 may be part of the controller 103 or operatively linked thereto.

As will be appreciated by those skilled in the art, various quantities of the modules 12 may be utilized with the address and data buses 101, 102, being adapted accordingly.

Although the circuit of FIG. 6 can establish the type of each module at each location and compare the results to a stored configuration for the intended prescription and therefore confirm the correct configuration of the correct modules, there remain technical challenges in the physical implementation of the data and address buses 101, 102.

In preferred embodiments, the address and data buses 101, 102 are ideally integral to the modules 12 themselves, not separate from them. Otherwise, module connections to separate buses would be required, requiring a substrate which would be the electronic equivalent of the tray in the nested designs. The requirement for a separate bus substrate would defeat the purpose and advantages of the serially-connected designs.

Figure 7:
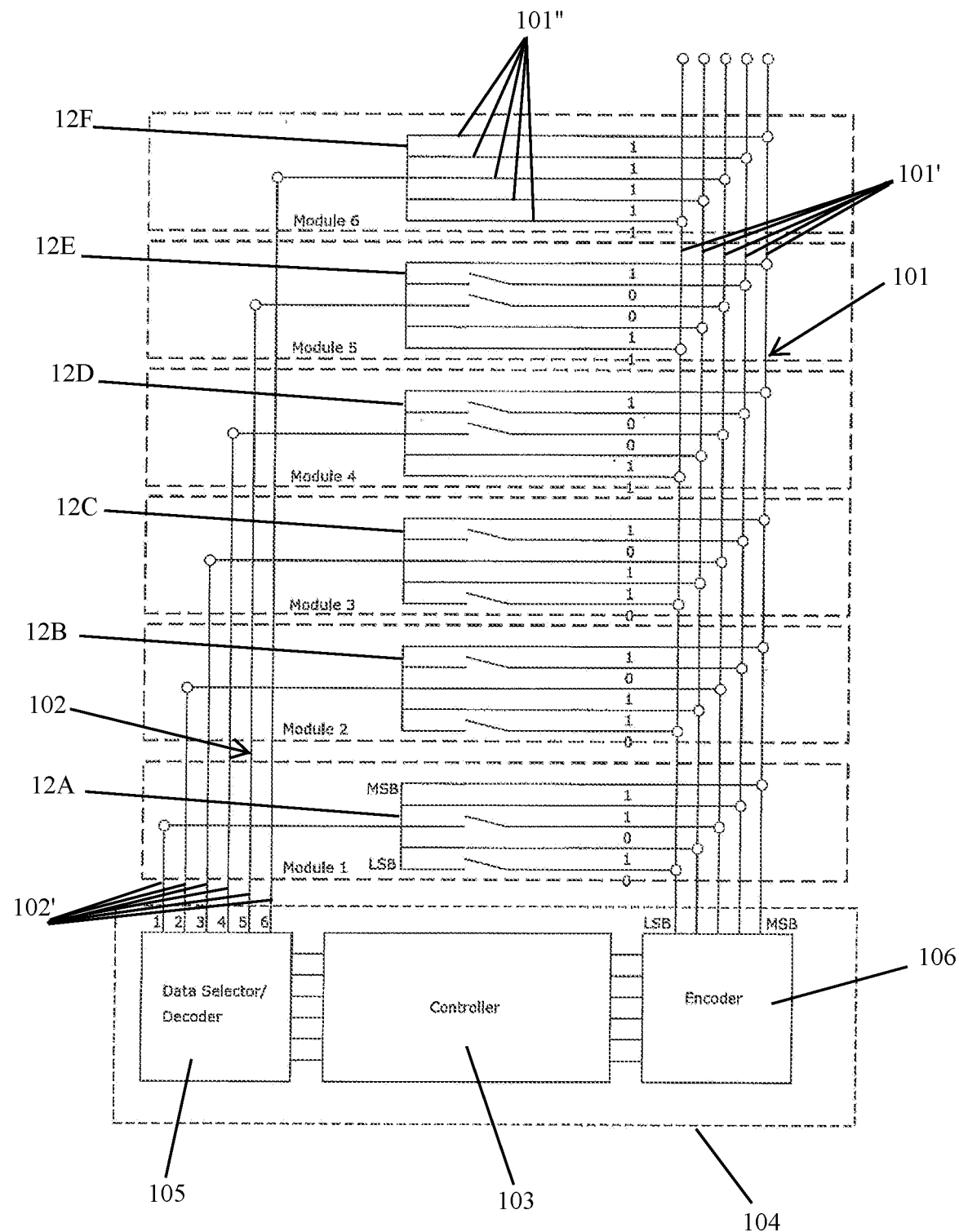
FIG. 7 is a schematic illustration of the circuit of FIG. 6 adapted such that the address and data buses are integrated into the module design.

In preferred embodiments, the buses 101, 102 are constructed as the modules are assembled together, by the connection of electronically conductive paths integral to the modules. In effect, the modules must provide and assemble their own data and address buses. Thus, regardless of the number of the modules 12 being utilized, a complete circuit is provided. This modification to the circuit of FIG. 6 is shown schematically in FIG. 7.

In the case of the data bus 101, construction of the data bus 101 is straightforward by connecting the modules 12 as the data transmission lines 101' are connected in series between the modules 12 in the data bus irrespective of the module's position in the assembly. The data bus 101 should include a quantity of data transmission lines 101' at least equal to the number of switches being used for each of the modules 12. Switch lines 101" are provided on each module 12 to connect each of the switches in one-to-one correspondence with the data transmission lines 101', for example, as shown with the module 12F in FIG. 6.

Physically, the data-bus 101 may be fabricated by means of wires embedded or bonded to the module housing or by conductive paints or films on the surface of, or embedded within, the module housing, by means of labels, or by any other appropriate means of creating conductive paths on molded articles that are known to the person skilled in the art.

In the case of the address bus 102, address lines 102' are provided on each of the modules 12 in a quantity at least equal to the number of the modules 12 in the assembly 10. The address lines 102' are axially connected in series with the modules 12 being connected.

It is preferred that each of the modules 12 be separately addressable. This can be achieved by electrically connecting each of the modules 12 to different address lines 102' so that the modules 12 are each uniquely in electrical contact with one of the address lines 102'. In this manner, the address lines 102' provide unique addresses for the modules 12. Stated differently, the address lines 102' correlate to the positions of the modules 12 in the assembly 10. The address line 102' to which a given module 12 is attached is dependent on the position of the module in the assembly.

In one variation, each of the modules 12 may be provided with a manually-adjustable electrical contact which allows for variably connecting with each of the address lines 102'. The manually-adjustable contact may be a slide contact, a dial contact, or any other position-variable contact which is capable of varying position to electrically contact each of the address lines 102' individually. The manually-adjustable contact is adjusted to electrically connect with the address line 102' corresponding to the position of the relevant module 12 within the assembly 10.

Preferably, the modules 12 are automatically electrically connected with the correct address line 102' passively, without a user doing more than connecting the modules 12. Any arrangement which allows for automatic electrical connection with the correct address line 102' may be utilized.

When using universality in the module design so that all modules are mechanically equivalent such that any module can in principle be assembled in any position, there can be no foreknowledge of the module's location stored in the module itself. For example, it is not possible to use external mechanical features of the modules to control connections to the address bus. Instead, the module connections to the address bus must be made in the field at the point of use.

In embodiments, this can be achieved by providing on each module an identical gang of switches and associated electronic conductors so designed that the switches and conductors on one module interface with those on neighboring modules to create electronic connections between the modules and the controller electronics. A key feature of this approach is that the controller housing likewise has an electronic connector to the first module in the assembly which is designed to connect, by switching means, the first module in the assembly to the first address bus transmission line. A further key feature is that once the first module is in position adjacent to the controller housing, by switching means, the assembly of the second module in the assembly automatically connects it to the second address bus transmission line, and so on for all subsequent modules. In embodiments, such an incrementing, sequential switching cascade may be achieved by means of pins and sprung type electronic connectors which are designed to increment and shift the active address bus transmission line depending on the position of the current module in the assembly. In this way, completing the assembly of modules simultaneously completes the address bus and the module connections to it. In other embodiments, non-mechanical solid state switching means may be employed e.g. capacitive switches, Hall effect sensors or any other suitable switching means known to the person skilled in the art.

Figure 8:
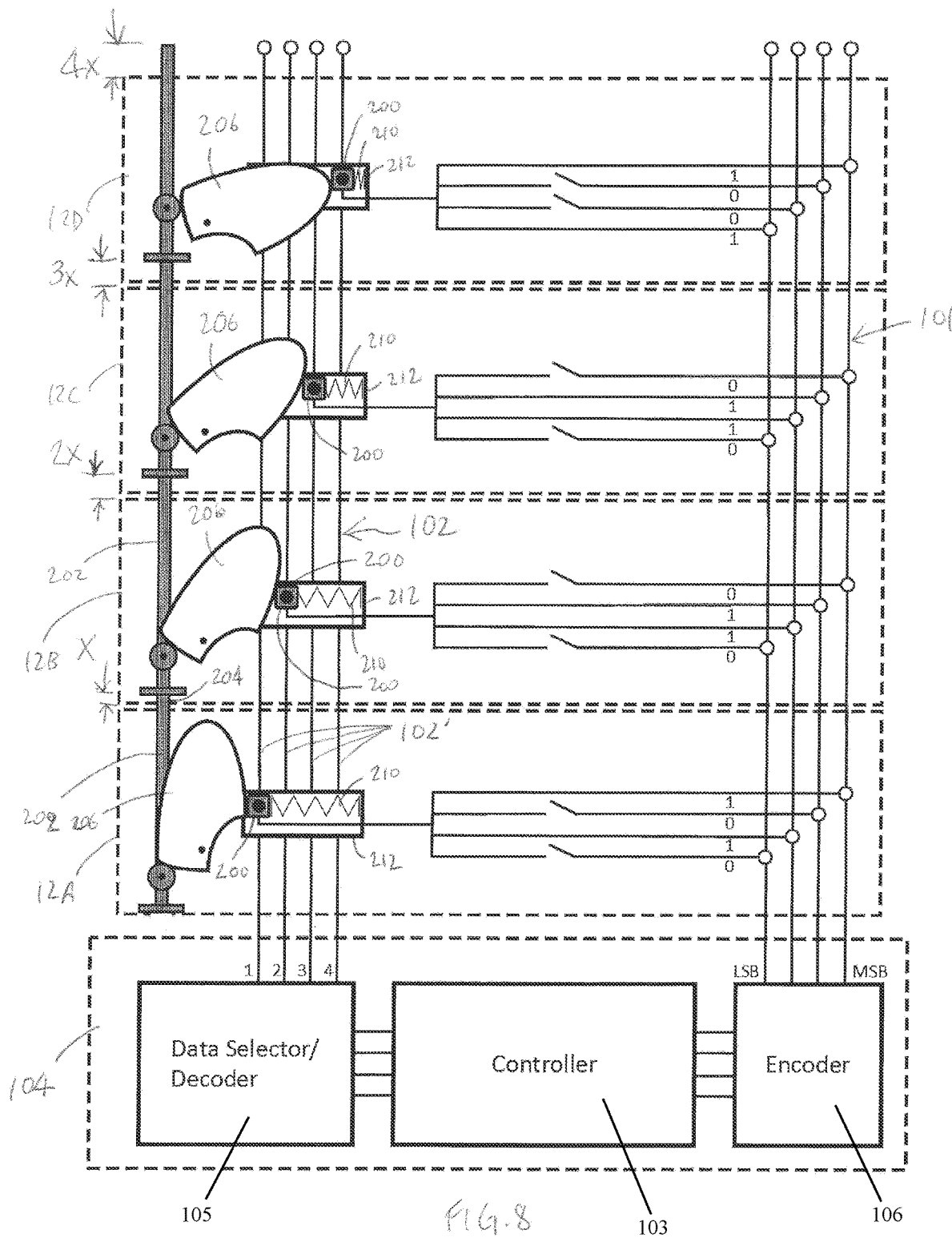
FIGS. 8-14 show different arrangements which allow for automatic mechanical address setting of a module on the proper address line in an address bus based on the module's location in an assembly.
Figure 9:
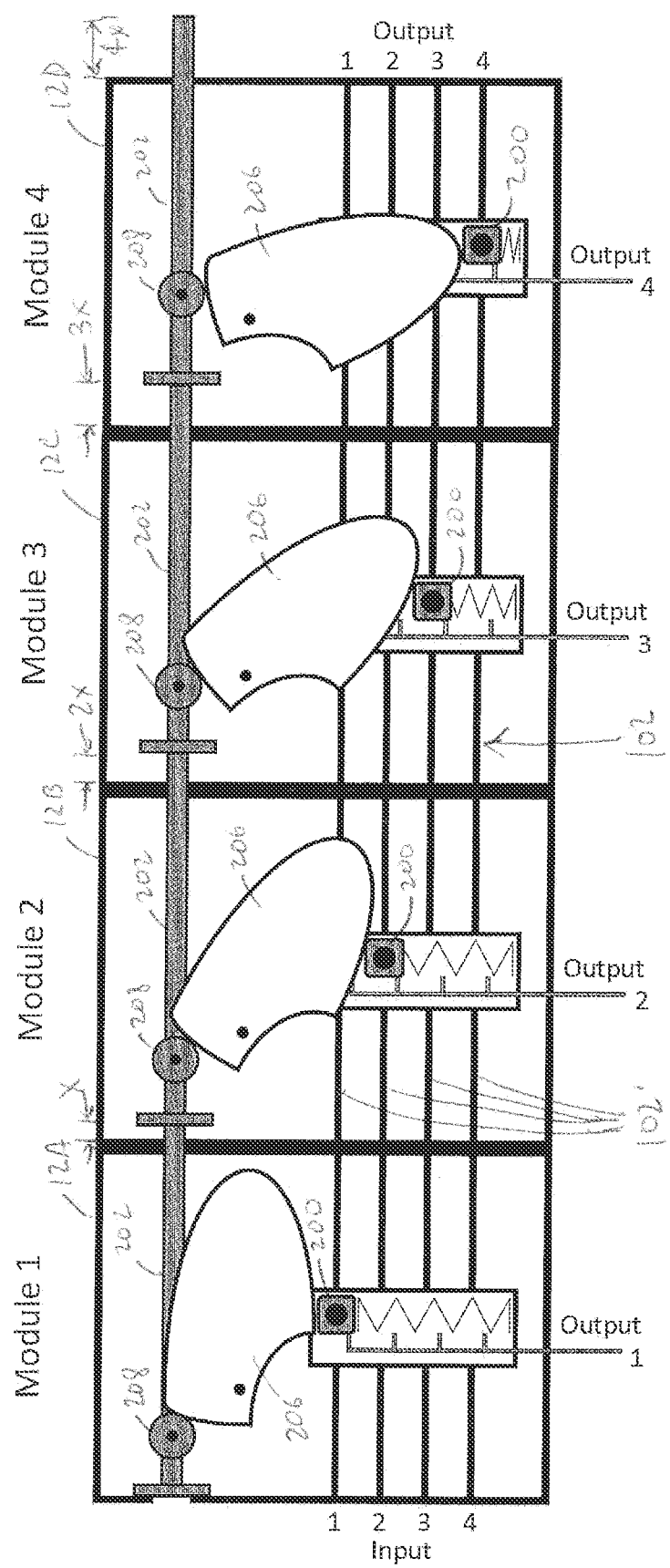
Figure 10:
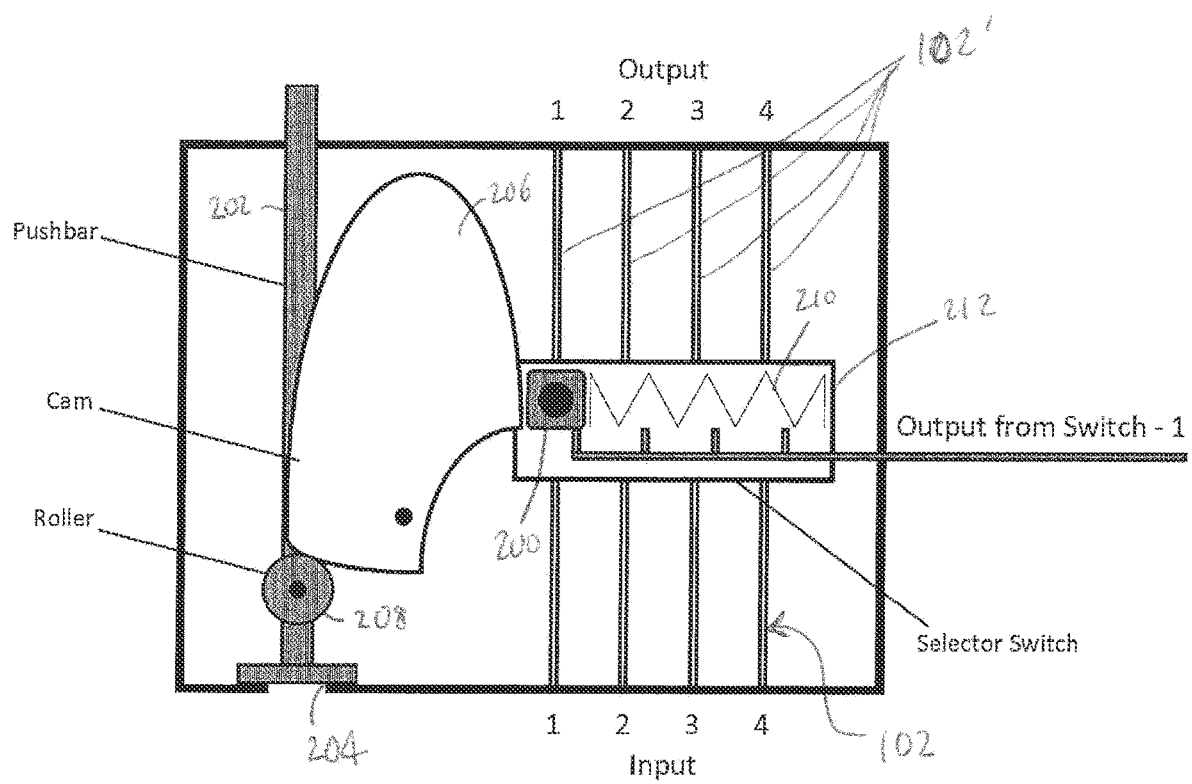

By way of non-limiting example, and with reference to FIGS. 8-14, arrangements are shown which allow identically-configured modules to be serially connected yet allow for adjustment of a contact 200 to connect to the proper address line 102' on the address bus 102. In particular, each of the modules 12 is provided with an axially-shiftable position pin 202 coupled with the contact 200 to cause adjustment thereof. The position pin 202 is sized to be greater in length than the width of the module 12 so that a portion extends a discrete length x from the module 12 in an initial state. With the first module 12 being connected to the controller housing 104, the position pin 202 is not caused to be displaced (i.e., remains in the initial position). All of the modules 12 are configured to have the position pin 202 be in the same initial position. In this position, the contact 200 is aligned to contact the address line 102' corresponding to the first module 12A being in the first position. With the connecting of a second module 12B to the first module 12A, the position pin 202 of the first module 12A is caused to extend into position channel 204 of the second module 12B, thereby causing the position pin 202 of the second module 12B to be axially shifted a distance x. Since the position pin 202 of the second module 12B was initially extending from the second module 12B a distance x, the axial shifting causes the position pin 202 to extend a distance 2x from the second module 12B. The position pin 202 in the second module 12B, as with all of the modules 12, is coupled to the contact 200 so that axial shifting of the position pin 202 causes movement of the contact 200 between the address lines 102'. As shown in FIGS. 8-10, the position pin 202 may be coupled with a rotatable cam 206. Rotation of the cam 206 causes movement of the contact 200. The cam 206 is configured so that for each displacement of the position a distance x, the cam 206 displaces the contact to the next address line 102'. With the arrangement of FIG. 8, the displacement of the position pin 202 increases with each subsequently connected module (e.g., 3x for the third module 12C, 4x for the fourth module 12D, etc.) with the contact 200 being aligned with a different address line 102' for each fixed displacement of the position pin 202 (e.g., the third address line 102" for the third module 12C, the fourth address line 102' for the fourth module 12D, etc.). The greater displacement of the position pin 202 results in greater rotation of the cam 206 with greater adjustment of the contact 200.

The position pin 202 may be coupled to the cam 206 in any known manner. As shown in FIGS. 8-10, a roller 208 may be provided on the position pin 202 arranged for non-fixed pressing engagement against the cam 206. With axial displacement of the position pin 202, the roller 208 presses against the cam 206 in causing rotation thereof. Other connections are possible, such as a pin connection to the cam 206.

A spring or other biasing member 210 may be provided within a housing 212 to act against the contact 200. The spring 210 is situated to urge the contact against the cam 206 to enhance engagement therebetween.

Figure 13:
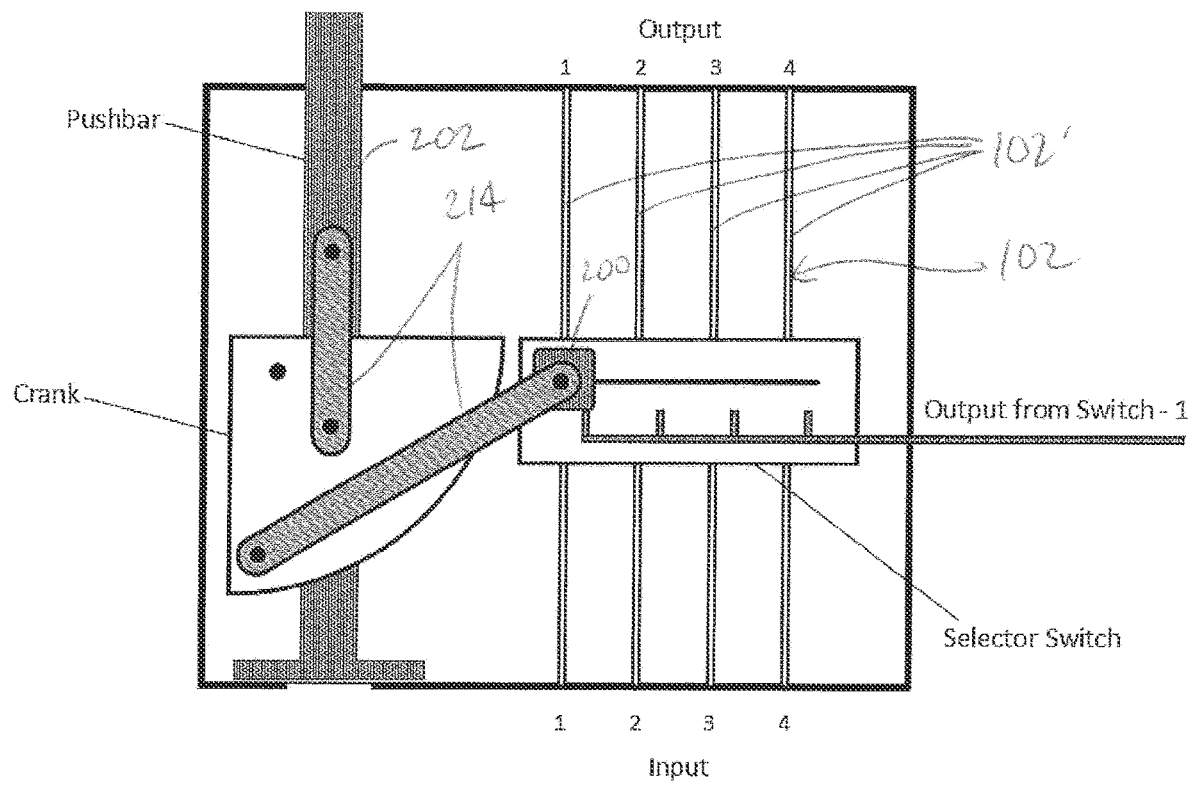
Figure 14:
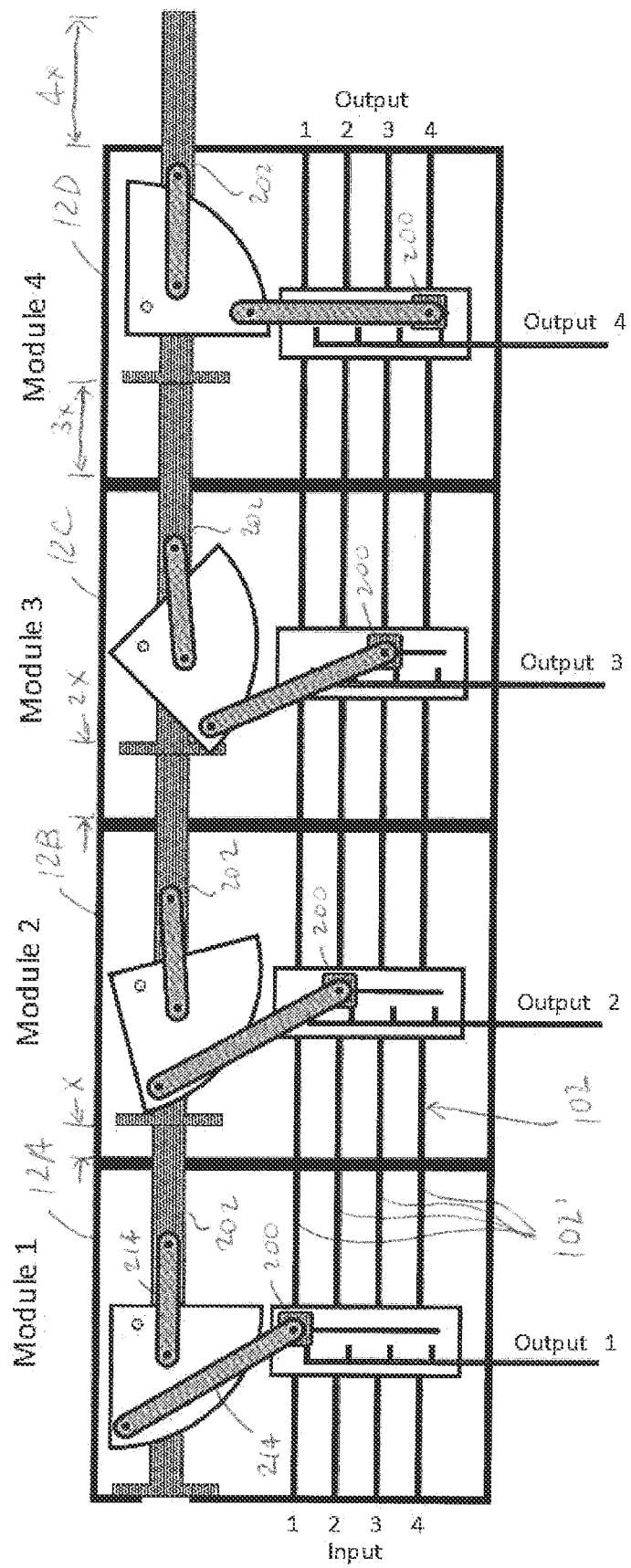

As will be appreciated by those skilled in the art, various elements and/or arrangements may be used in place of the cam 206 to translate the axial movement of the position pin 202 into displacement of the contact 200. For example, as shown in FIGS. 13-14, a combination of links 214 may be used arranged to displace the contact 200 in response to axial movement of the position pin 202, particularly, in a fixed relationship where for each x displacement of the position pin 202, the contact 200 is adjusted to a different address line 102'.

Figure 11:
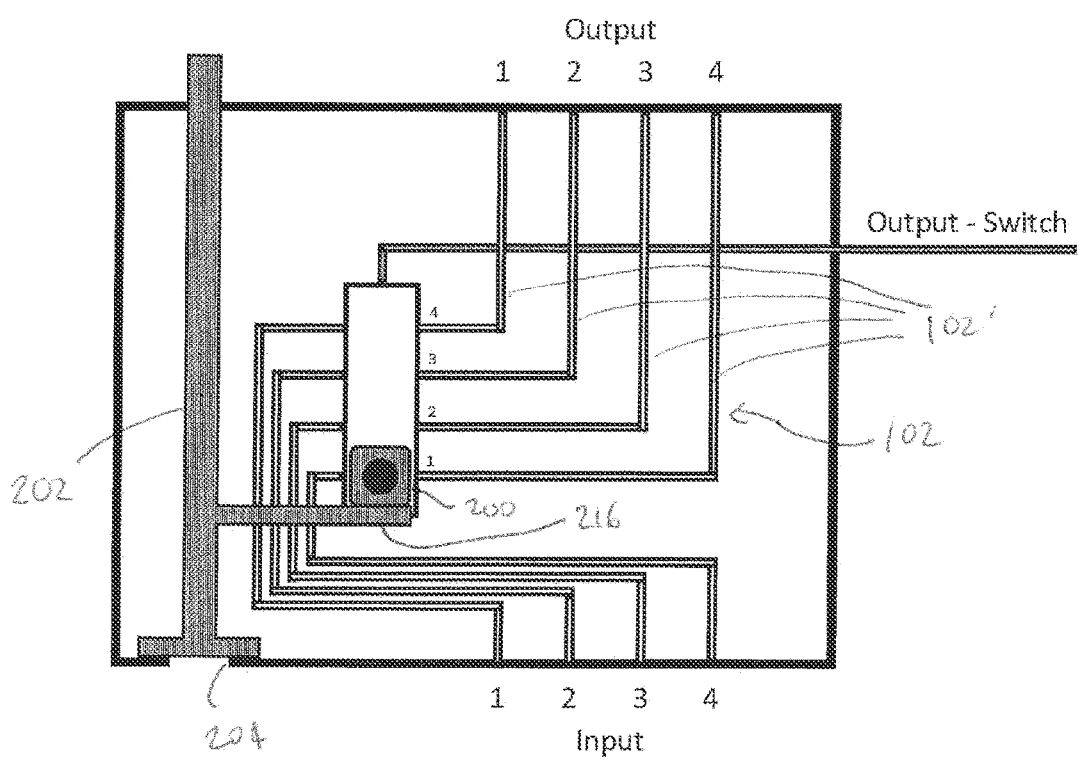
Figure 12:
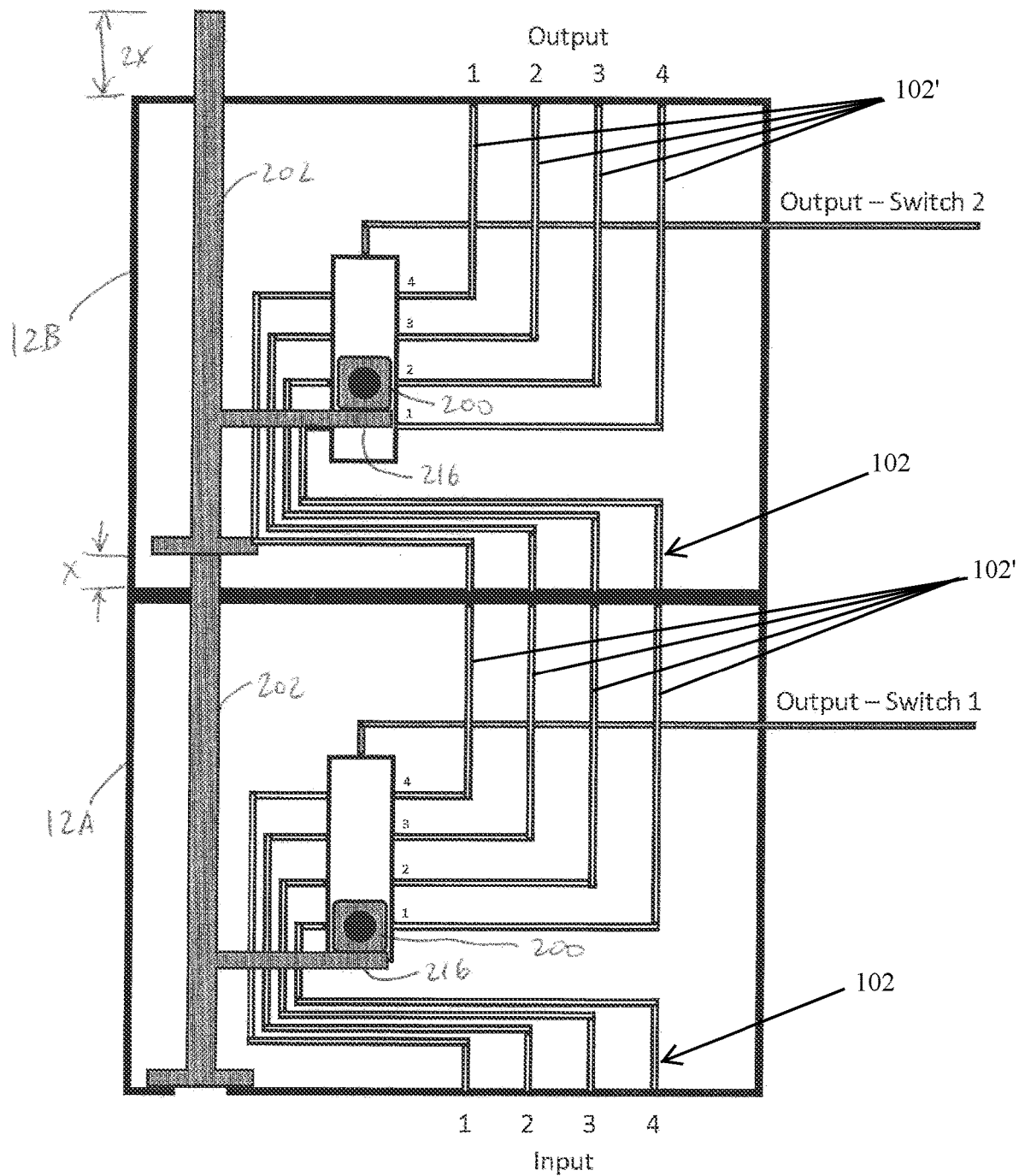

As shown in FIGS. 11-12, it is also within the scope of the invention to couple the contact 200 to the position pin 202 with a rod 216 so that the contact 200 moves in concert with the position pin 202 (e.g., along a parallel axis). Here, the contact 200 is displaced the same distance as the position pin 202. The distance x of each incremental displacement is equal to the spacing between the address lines 102'.

Figure 23:
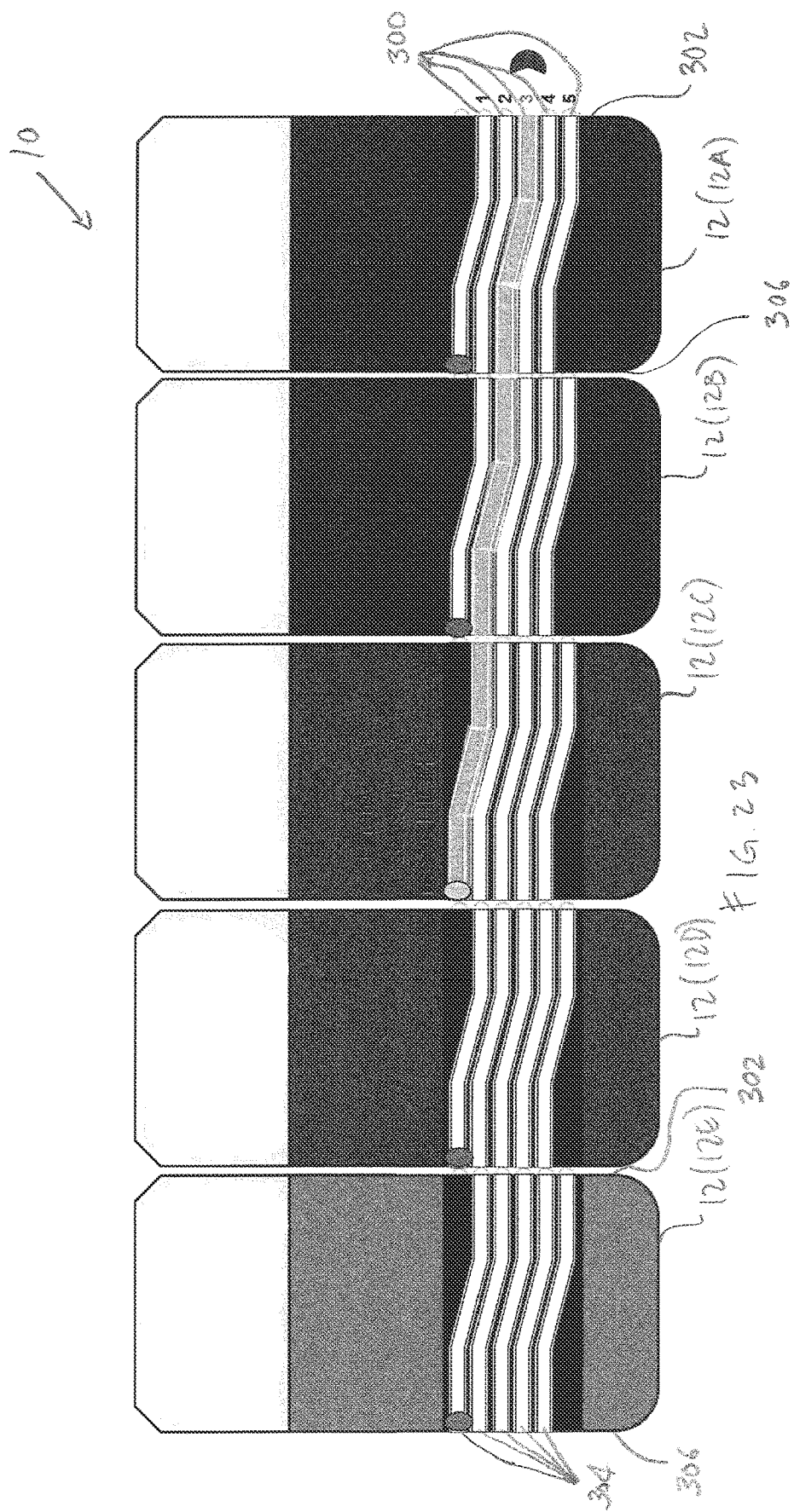
FIGS. 23 and 25 demonstrate the lane-shifting electronic connections between modules.
Figure 24:
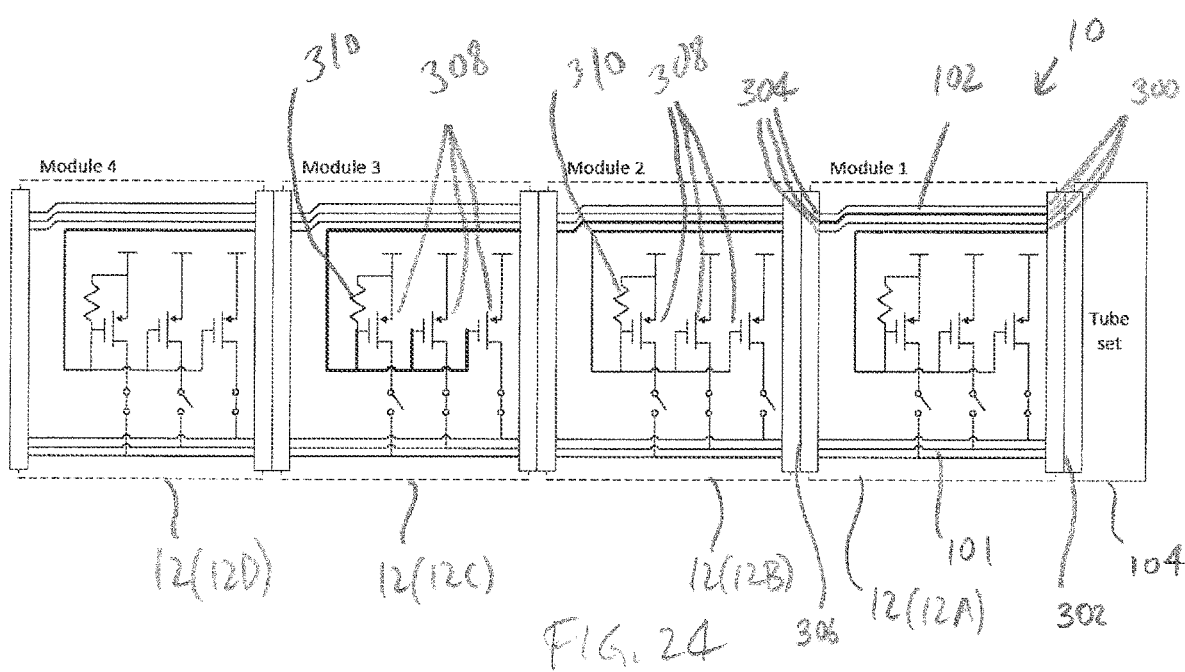
FIG. 24 is a schematic showing the lane-shifting connections with an error-detection system composed of resistors and MOSFETs.
Figure 25:
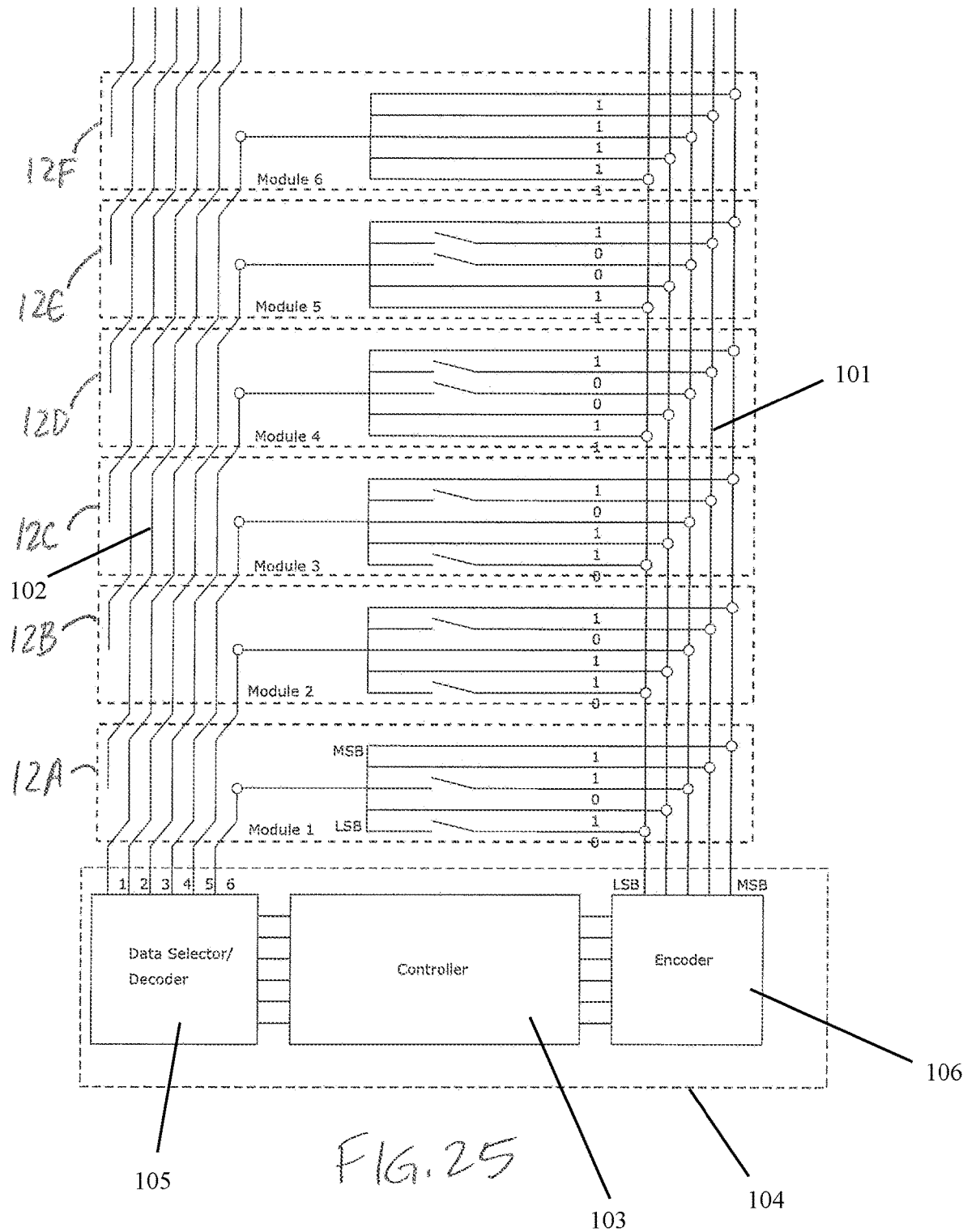
Figure 27:
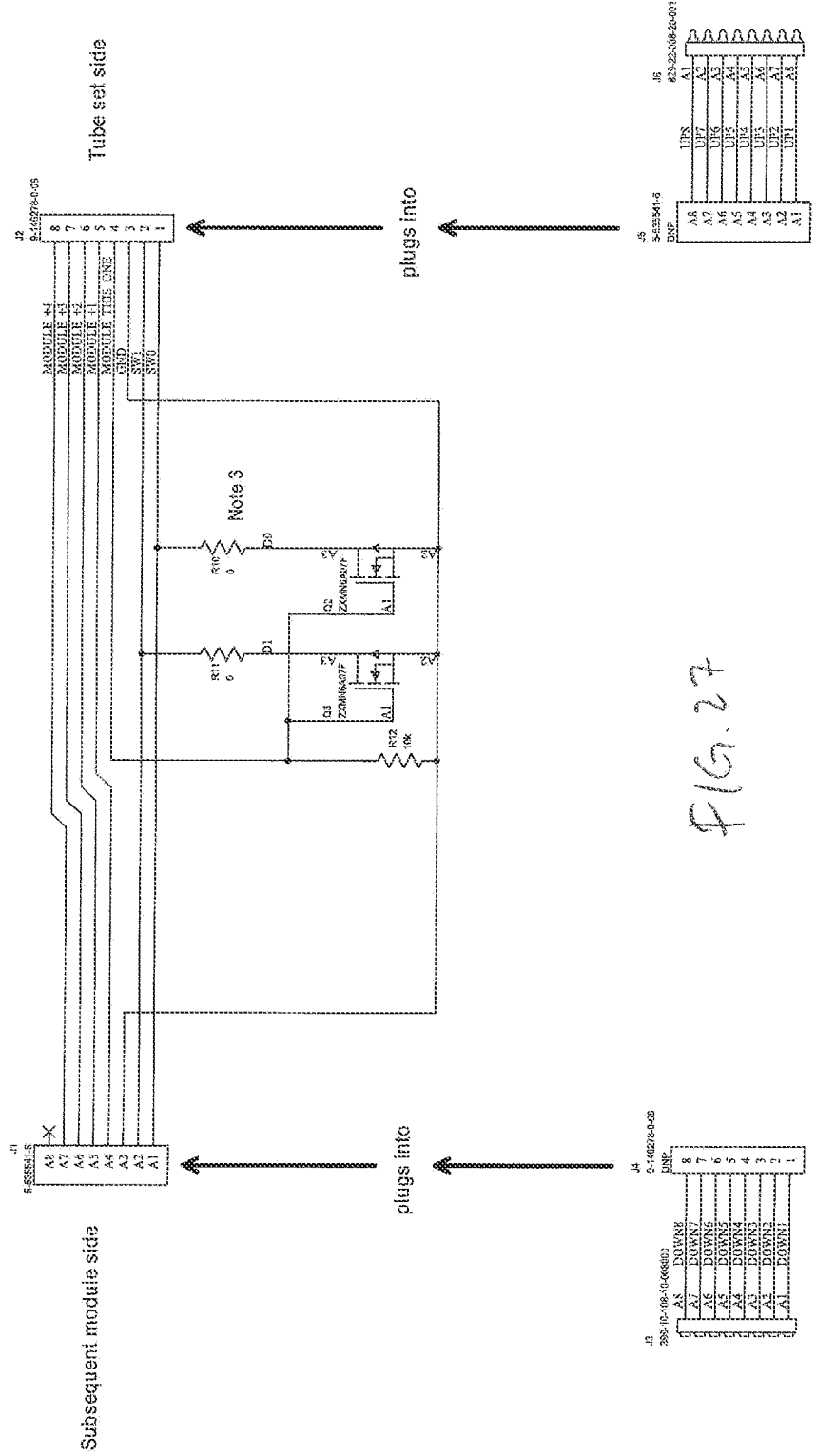
FIG. 27 is a schematic of electrical circuitry useable with any of the lane-shifting electronic connections.

In an alternative embodiment, as shown in FIGS. 23-25, the address bus 102 may be defined by a series of parallel conductors provided in each of the modules 12. This allows for the modules 12 to be identically configured. As shown in FIGS. 23-25, the electrical conductors are arranged to not have ends be axially aligned. In this manner, for each of the modules 12, first ends 300 of the electrical conductors may be located along a first face 302 of the module 12 with second ends 304 of the electrical conductors being located along a second face 306 of the module 12. The first ends 300 and the second ends 302 are out of phase by one increment such that the first ends 300 and the second ends 304 of adjacent modules 12 overlap in a relationship of n−1 so as to be directly couplable (e.g., with five electrical conductors, four will overlap for direct coupling). This allows for continuous pathways to be defined from the first face 302 of a first module 12A, to each of the other modules (12B, 12C, . . . ) along separate conductors. This allows for serially addressing each individual module 12 by addressing each of the conductors individually. Thus, for example, as shown in FIG. 23, the first end 300 of the module 12A labelled 1 provides an addressable connection for the module 12A. The first end 300 labelled 2 provides an addressable connection for the second module 12B, the first end 300 labelled 3 provides an addressable connection for the third module 12C, and so forth. The number of electrical conductors must be at least equal to the number of modules 12 in the assembly 10. The electrical conductors may be formed to conduct electricity, but also be light conductive, if light is being used for addressing the modules 12. In addition, as an alternative, as shown in FIG. 26, the conductors may be provided on a substrate, such as a printed circuit board (PCB), e.g., as traces, where the first ends 300 and the second ends 304 are aligned in the same manner as described above. The conductors may be configured to be the full length, or, alternatively, less than the full length, of the printed circuit board. As discussed below, the printed circuit board can be included with the modules 12 in any manner, including overmolding or other assembly. With a printed circuit board configuration, jumpers or other connectors may be used to connect the conductors with external portions of the modules 12 for connections between the modules 12, as shown schematically in FIGS. 25 and 28 with lines extending from the ultimate module 12, 12F. FIG. 27 schematically shows a possible substrate (e.g., PCB) circuitry arrangement useable with the electrical conductors as arranged in any of FIGS. 23-26.

With reference to FIG. 24, the data bus 101 may be formed in similar fashion to that described above. FIG. 24 shows a circuit useable on each of the modules 12 which includes a MOSFET 308 in series with each of the switches. Power may be provided to each of the MOSFET's 308 through one or more resistors 310. This allows for addressing the individual switches within each of the modules 12.

Similarly to the data bus 101, in any embodiment herein, physically, the address lines 102' of the address bus 102 may be fabricated in the modules 12 by means of wires embedded or bonded to the module housing or by conductive paints or films on the surface of, or embedded within, the module housing, by means of labels, or by any other appropriate means of creating conductive paths on molded articles that are known to the person skilled in the art. In addition, or alternatively, the address lines 102' may be defined by traces and/or conductors on a printed circuit board or other substrate which is incorporated into the modules 12, e.g., by overmolding or other assembly.

Figure 15:
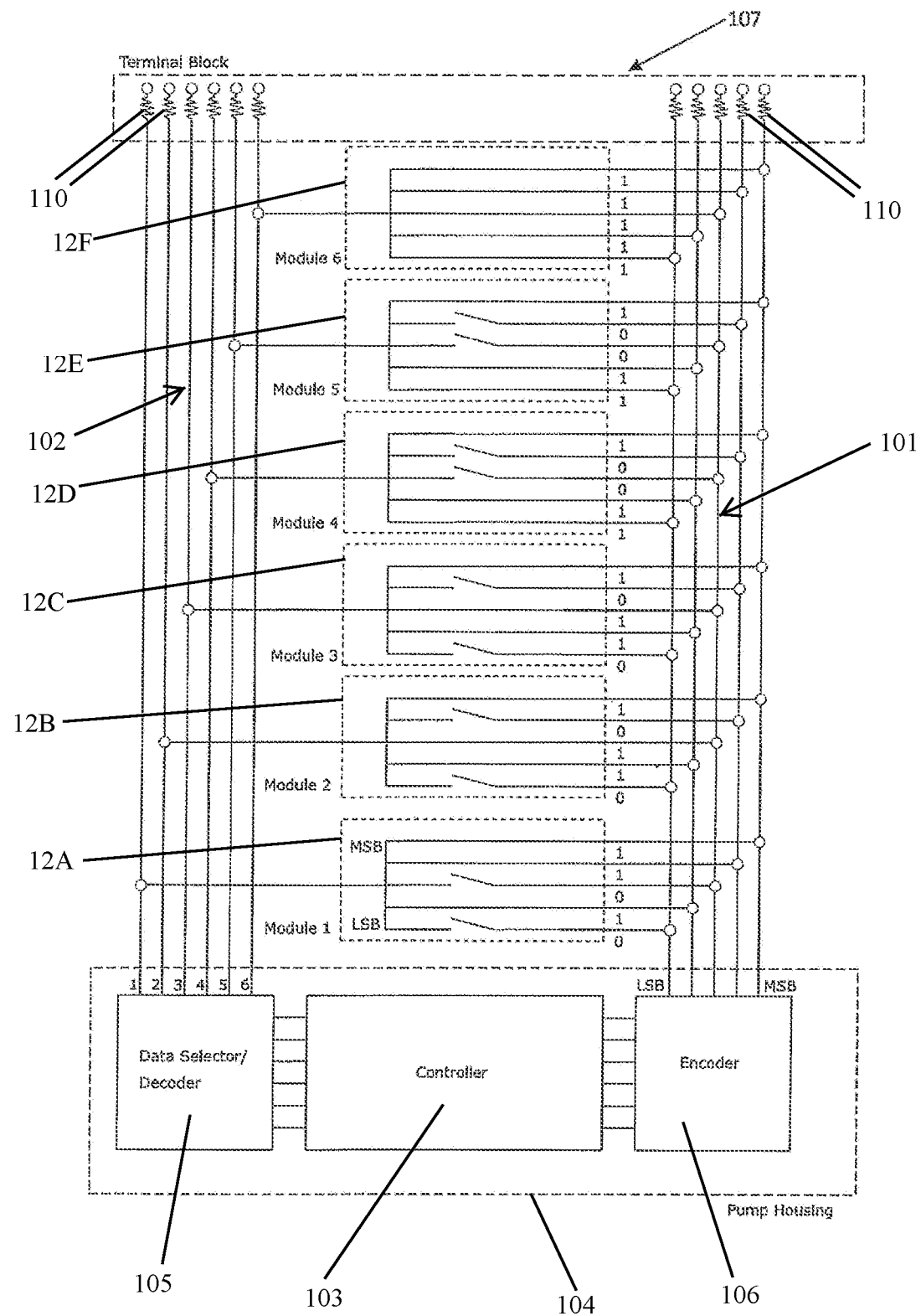
FIG. 15 is a schematic illustration of the circuit of FIG. 6 with a terminal block component incorporating terminal resistors to provide electronic termination of the address the data buses.
Figure 16:
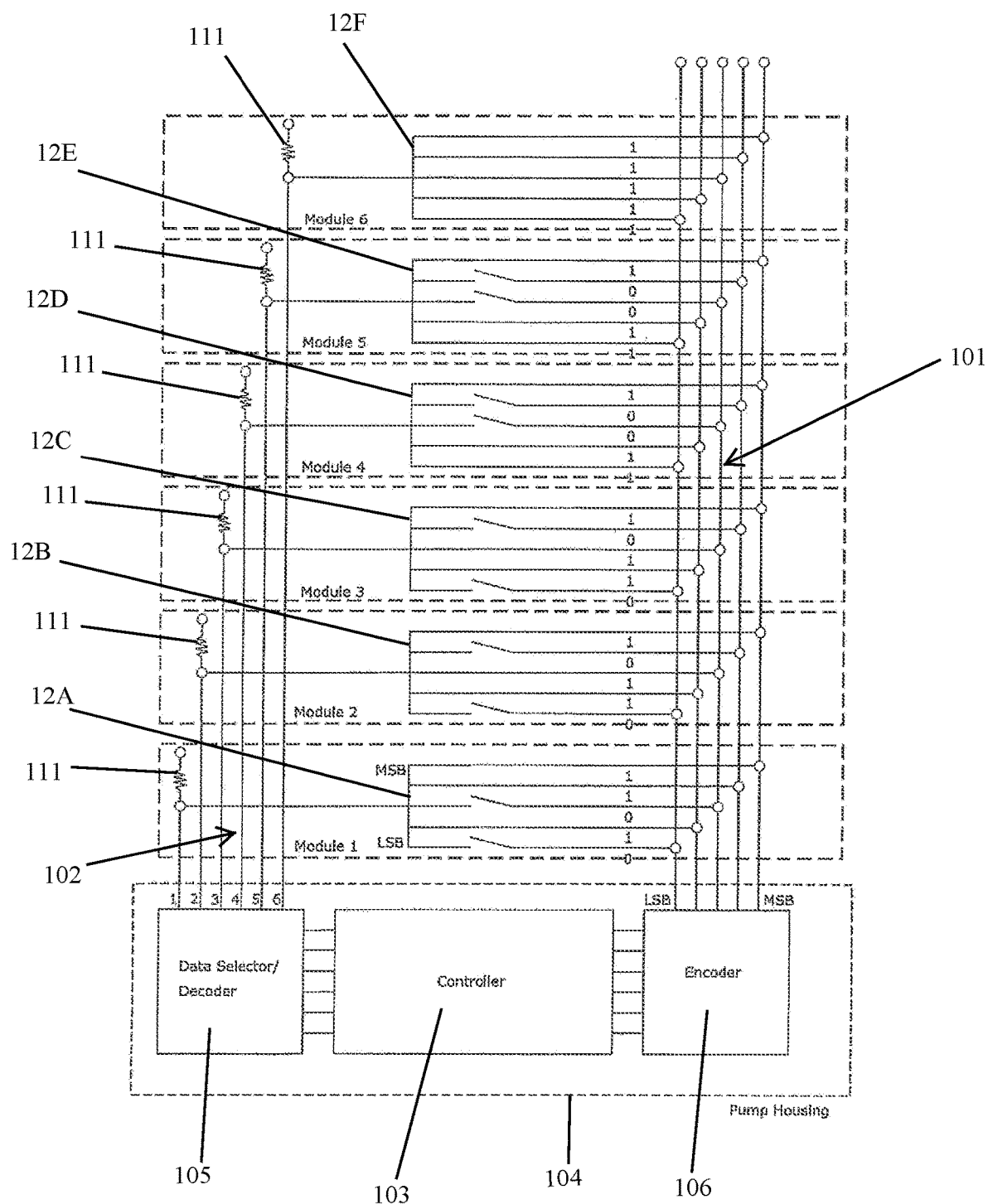
FIG. 16 is a schematic illustration of the circuit of FIG. 7 in which the bus terminating resistors are built into the modules.

It will be understood by the person skilled in the art that depending on the details of the circuit design, some additional circuit elements such as pull-up or pull-down resistors to ensure the correct logic levels, bus termination resistors and so on may be required on both the address and data bus sides of the circuit. In embodiments such additional circuit elements, such as bus termination resistors 110, could be provided in a terminal component, 107 (FIG. 15), built into the controller housing 104 or built into the modules 12 themselves. In the latter case, each module 12 could have an integrated terminal resistor 111 for example. The sequential switching cascade described above could then be so designed such that the resistor is connected to terminate the bus lines automatically by the last module in the assembly. This is shown schematically in FIG. 16.

Figure 17:
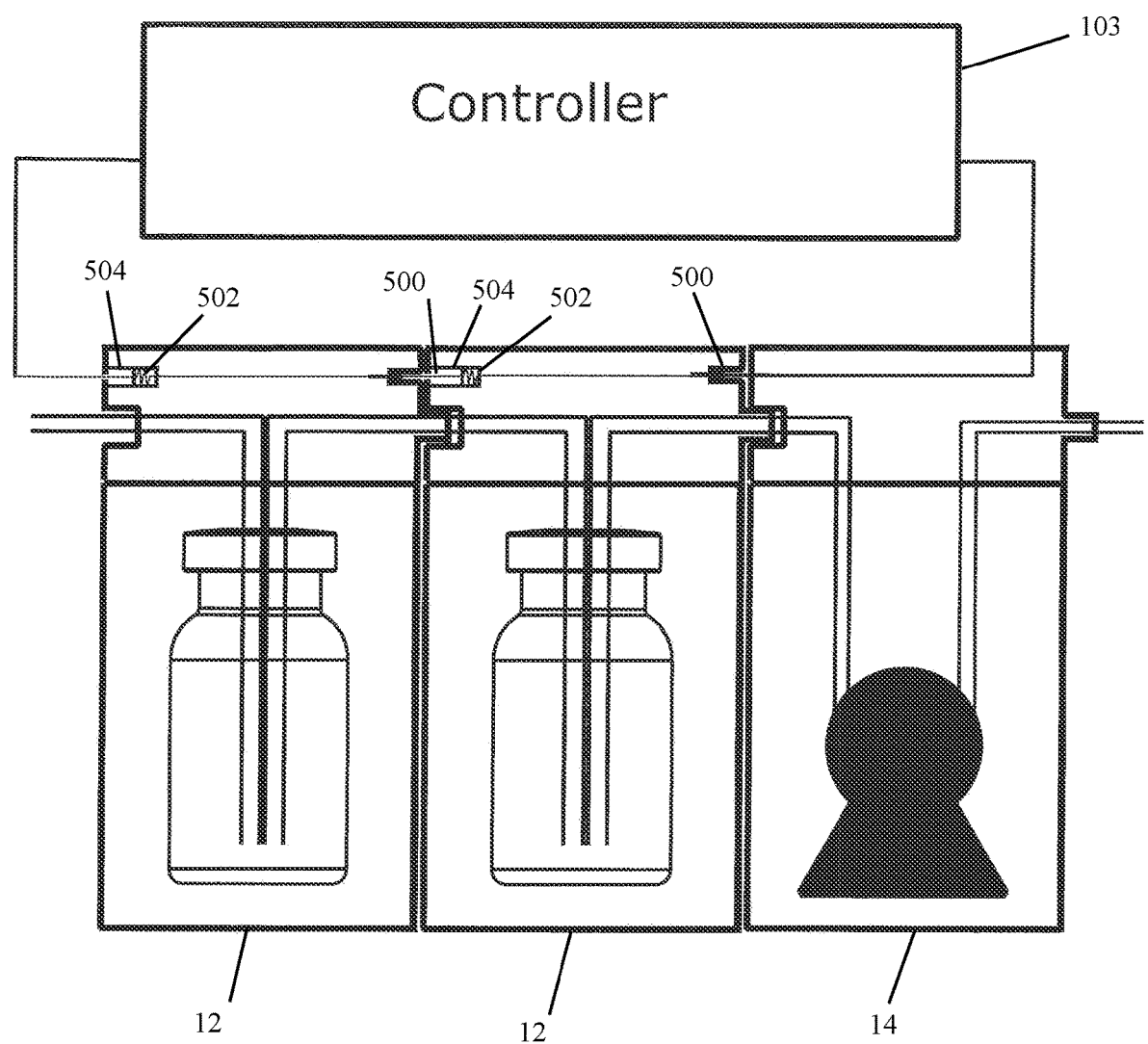
FIGS. 17, 18A, 18B, 20A, and 20B show various additional features useable with the subject invention.

The electronically serially-connected assembly according to the present invention has several advantages. One potential advantage is that the need to make physical electronic connections can also be used to confirm that mechanical and fluidic connections have been correctly made. For example, as shown and described in FIG. 17, the system can be designed such that the electronic circuit is only completed when the fluid connections have been correctly made. For example, as shown in FIG. 17, conducting pins 500 may be provided on the modules 12 formed to electrically couple with spring contacts 502, located in recesses 504, upon sufficient insertion of the conducting pins 500 into the recesses 504. This ensures that the modules 12 are sufficiently proximate to ensure proper connections therebetween, both fluidically and electrically.

Figure 18A:
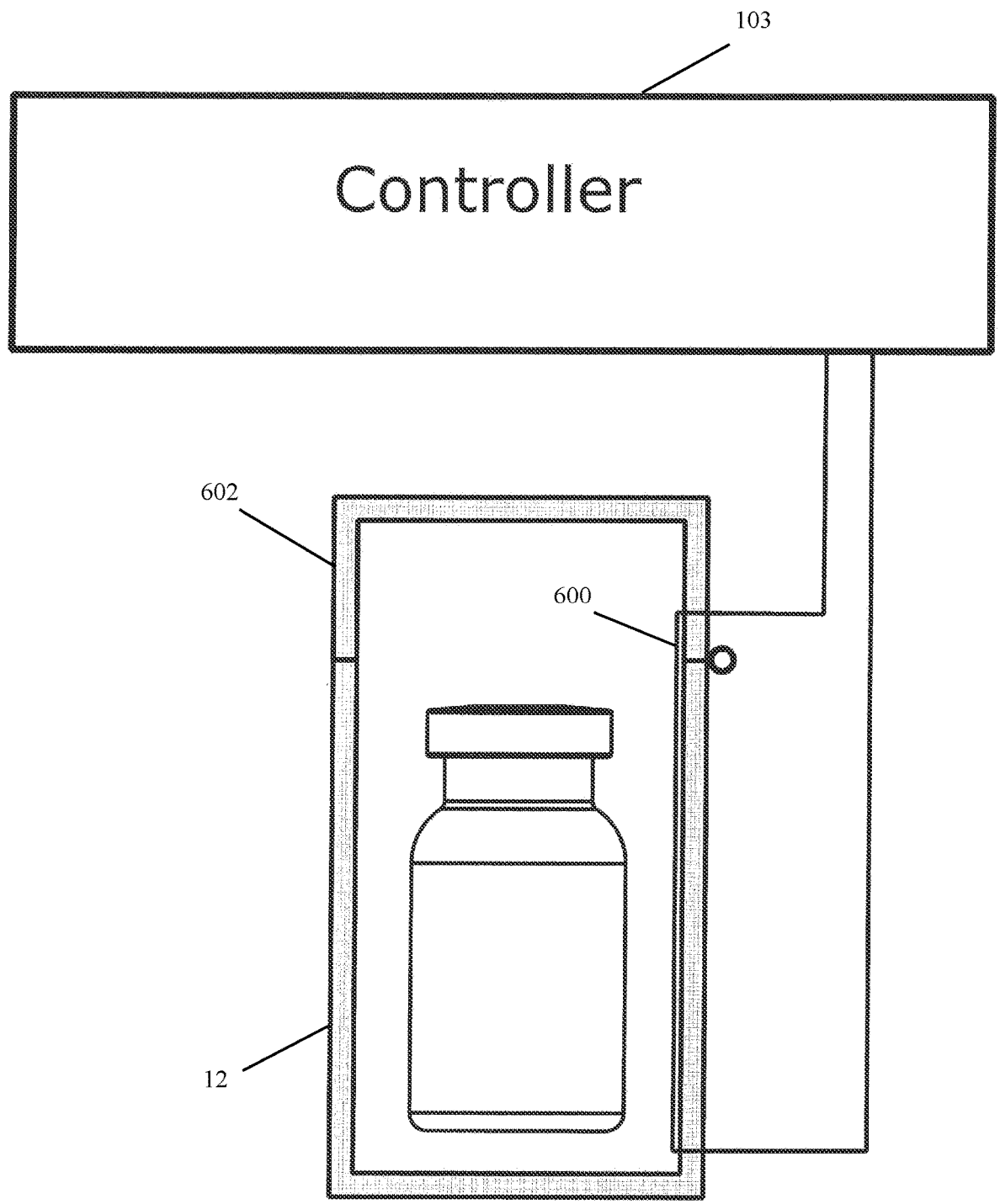
Figure 18B:
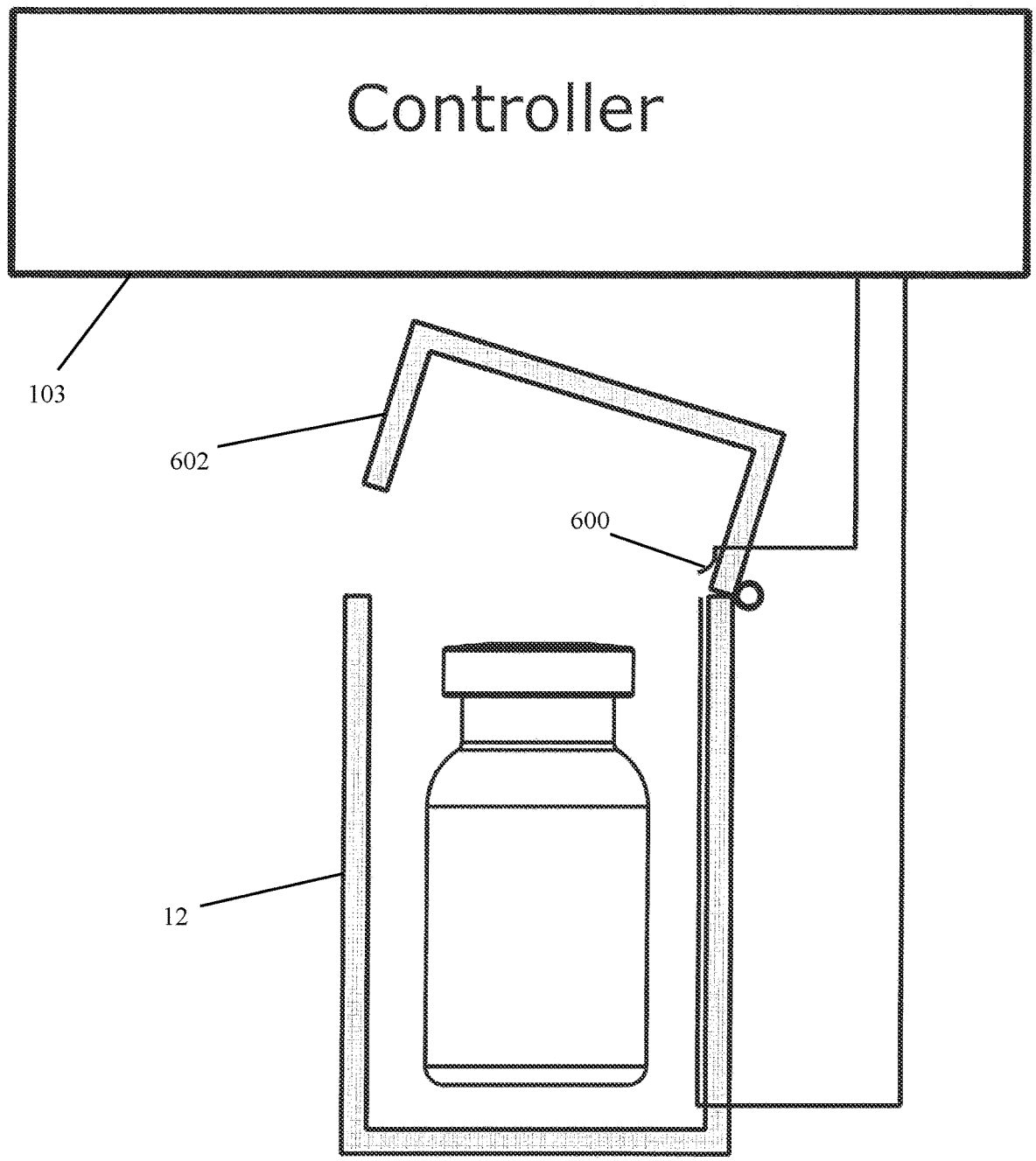
Figure 19:
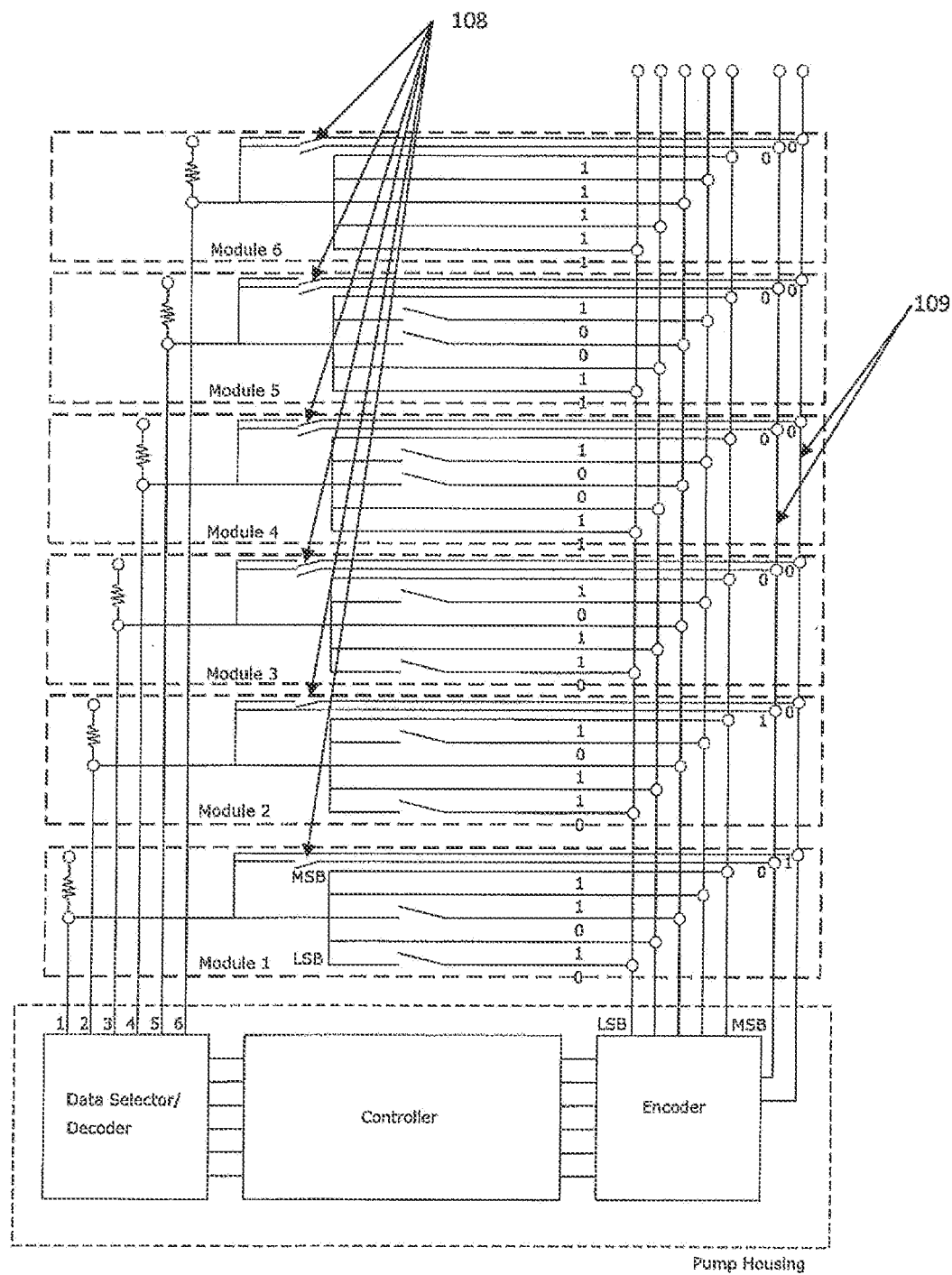
FIG. 19 is a schematic illustration of the circuit of FIG. 16 with two additional ancillary switches per module and additional data bus lines for status indicators, e.g. microswitches to indicate connection status.
Figure 20A:
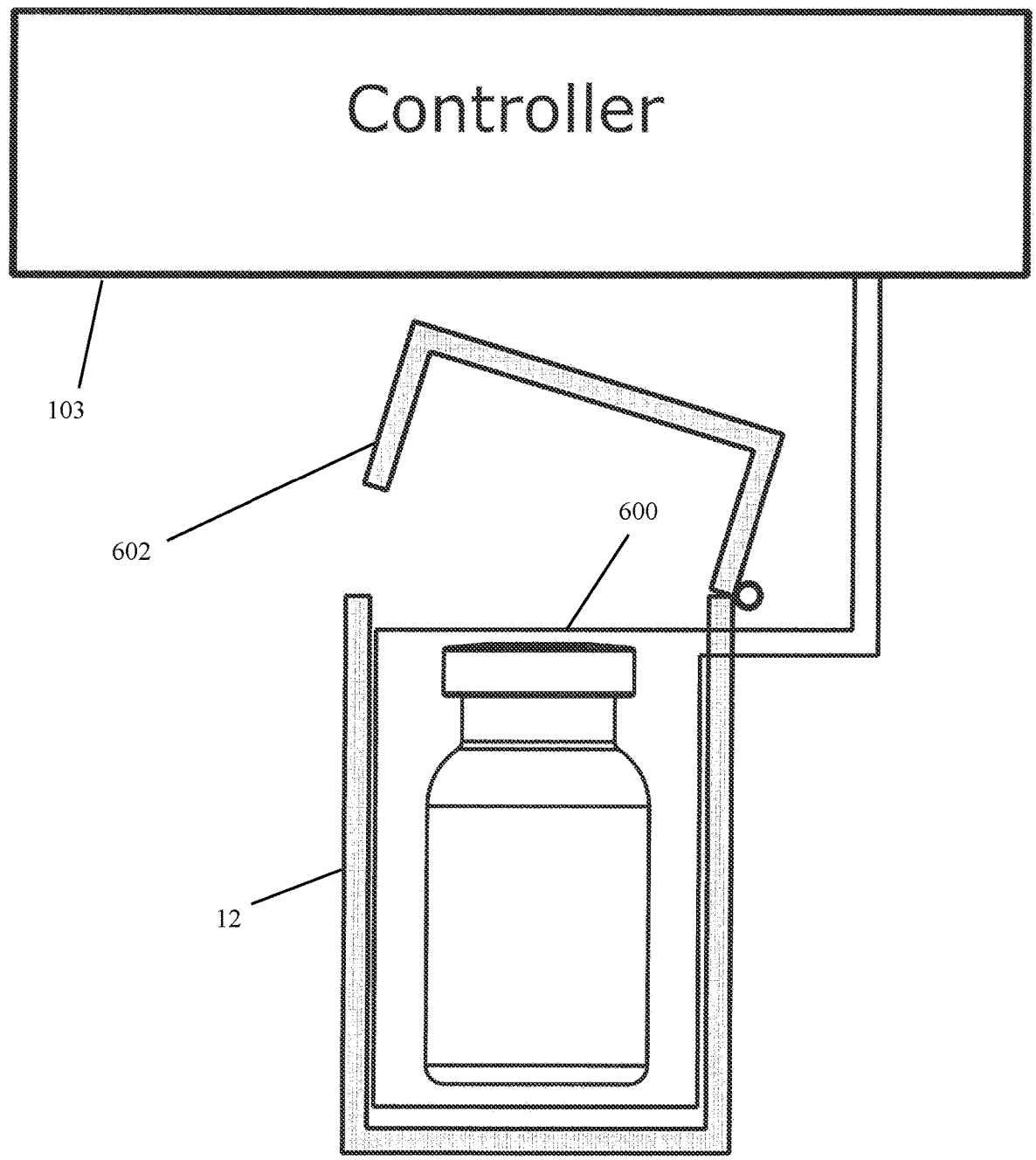
Figure 20B:
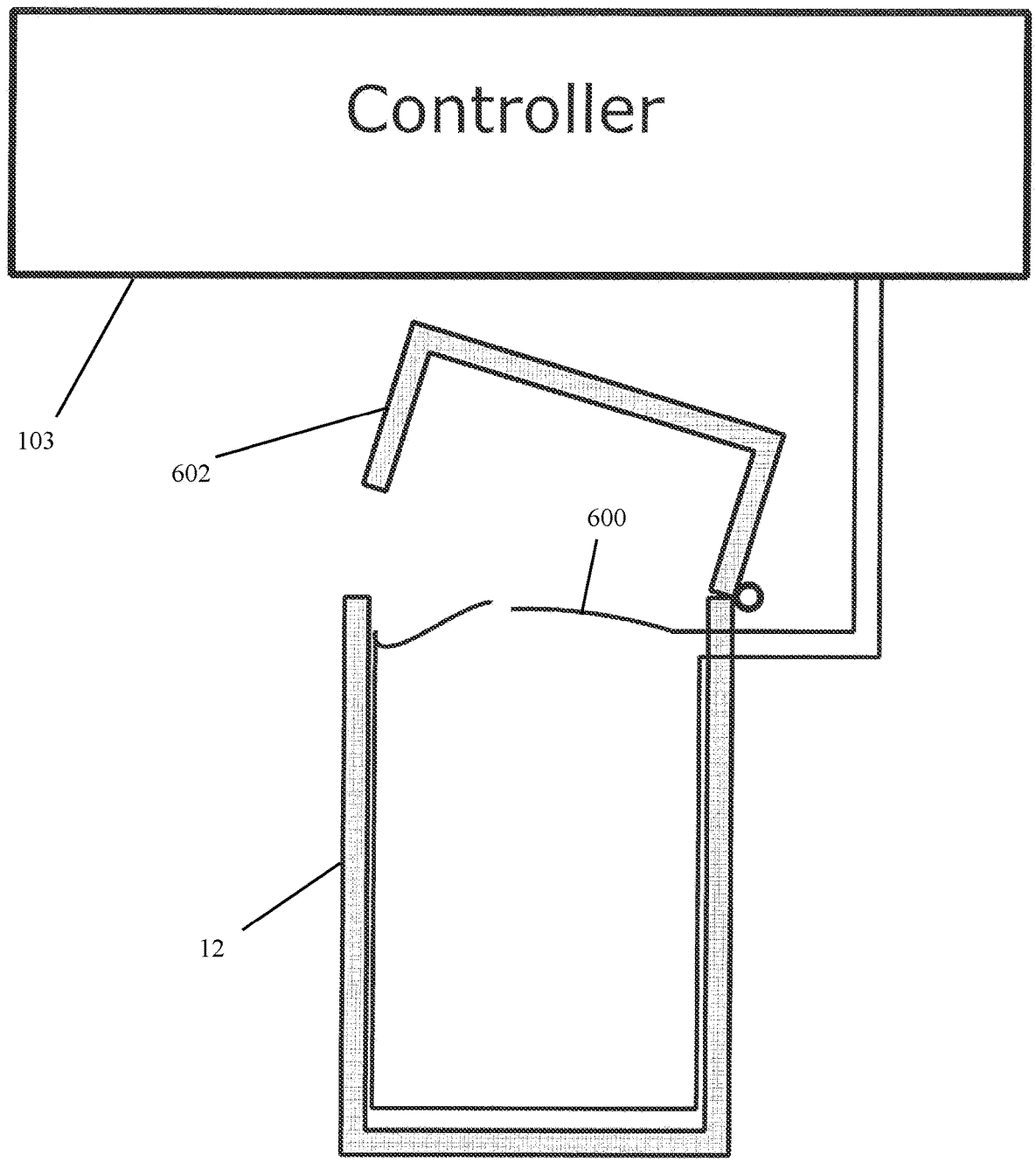

The use of electronics also enables the implementation of further error-prevention and status indicating features. For example, by addition of extra transmission lines to the data bus, the electronic logic circuit could interrogate additional binary status indicators on each module. For example, additional micro-switches 600 could be included in the modules 12 to indicate their connection status to other modules 12. For example, the switch 600 could be configured to be open when the module 12 is unconnected to other modules 12, and closed when it is assembled in an assembly. Similarly, a further status feature could indicate if the module cap 602, which is present to allow swabbing of the vial septum, is open or closed. This latter status indicator could be designed to be switchable/resettable or permanently set once the cap 602 has been opened or closed or a peel-able seal removed, e.g. as a use or tamper evident indicator. The latter effect could be achieved for example by arranging for the opening or closing of the cap to permanently breach an electronic conductor. In embodiments, multiple status switches could be implemented by means of multiple breakable conductors. That is, as shown and described in FIGS. 18A-18B, a switch 600 could be permanently set on opening the module cap 602 to indicate it has been opened. The switch 600 may be formed to extend along a wall of the module 12. A second switch could be permanently set on peeling of a peel-able film. A third switch could be set by closing the module cap 602. By suitable logical circuit design the status of these switches 600 could be interrogated to confirm that the cap 602 has been opened, the vial exposed for septum swabbing, and the cap 602 subsequently closed to pierce the septum. Further, as shown and described in FIGS. 20A-20B, a tamper evident arrangement could be provided, where the switch 600 provides indication of possible tampering with the contents of a module 12. Here, the switch 600 extends across the vial, rather than along a wall of the module 12, as shown in FIGS. 18A-18B. FIG. 19 shows the circuit of FIG. 16 with additional switches, 108, in parallel with the 5-gang module ID switches and two additional data bus lines, 109, which could be used for applications, e.g., to provide a status signal to the controller e.g. for assembly verification.

Figure 28:
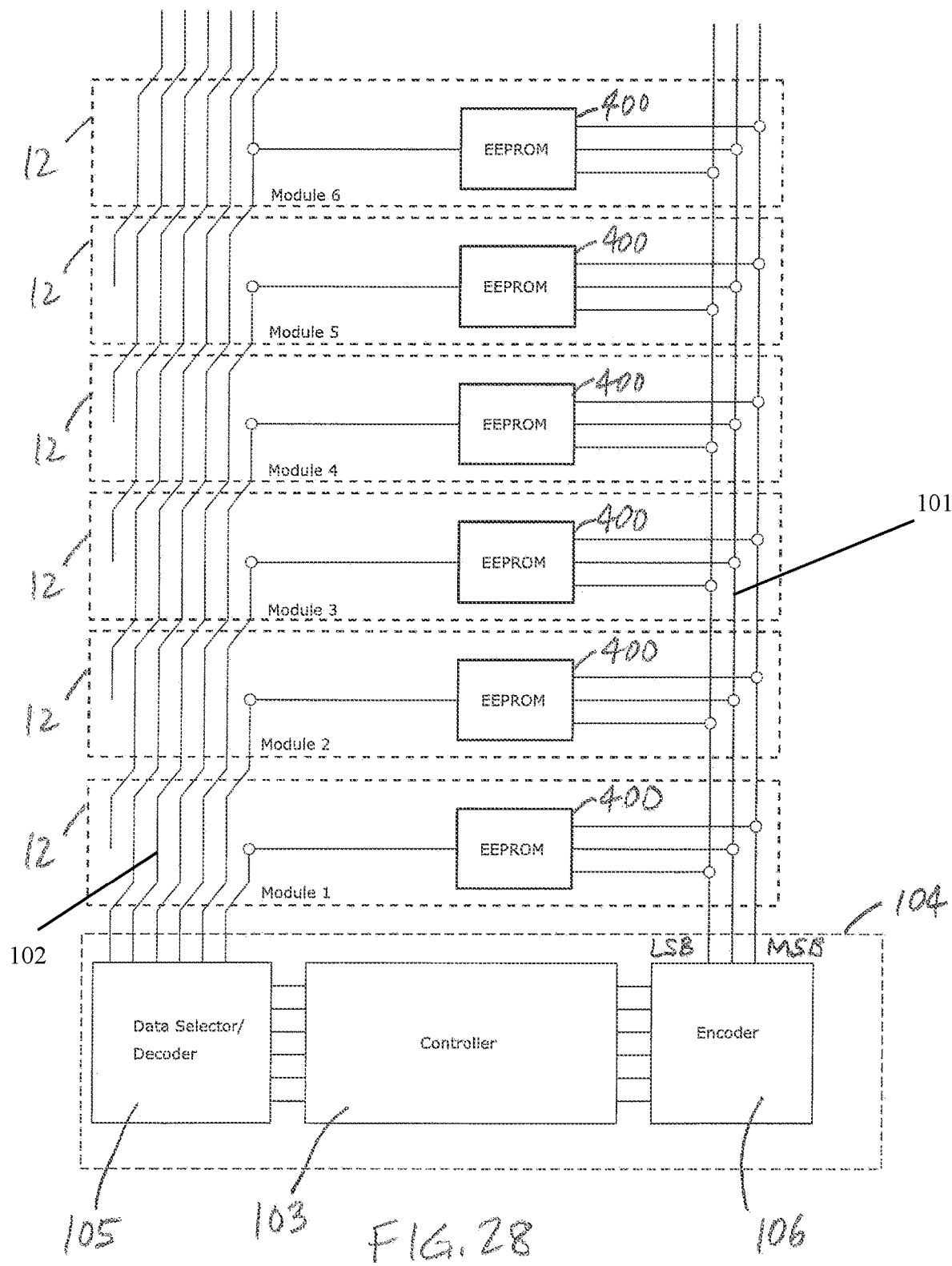
FIG. 28 is a schematic showing the use of a persistent memory with each of the modules.

With reference to FIG. 28, the modules 12, in any of the embodiments described herein, may be each provided with a persistent memory 400, such as an EEPROM memory. The memory 400 advantageously allows for storage of various readable data, including, but not limited to, data related to the associated drug, such as drug name, batch number, serialization code, expiration date, and so forth. In addition, security codes may be stored on the memories 400 to prevent counterfeiting. The memories 400 of the modules 12 may be interrogated using the address bus 102 in the same manner as discussed above. In addition, the memory 400 may be erasable/writable to allow for data stored therein to be updated. The memories 400 may store identifying codes for each of the modules 12 which are readable to function like the binary codes described above.

In addition, the modules may be configured to prevent reusability. For example, a fuse may be provided with each of the modules which is caused to break upon completion of dose administration, e.g., with a sufficiently large electrical pulse being emitted from the controller housing. The fuse may be provided along an electrical conductor (e.g., as a frangible element) and/or separately provided, e.g., as a chip which may be caused to break, thus, preventing electrical flow. In addition, or alternatively, the memory 400 of each of the modules 12 can act as a fuse in not allowing electrical flow when being erased. The memory 400 may each include a simple logic scheme which permits electrical flow such that, with removal of the scheme, electrical flow is prevented. For example, the memory 400 may be provided with a code indicating "ready for use" with the code being updated, post-use, by the controller housing 103 to a code indicating "used." Further use of the related modules 12 will have a "used" reading, preventing re-use.

In embodiments, an electrically powered transfer pump may be integrated into the pump housing. In embodiments, operation of said pump can be arranged to be under the control of the controller such that the pump can only be switched on to perform the drug transfer once the correct module identity, module status and system configuration has been confirmed.

Other status indicators can be conceived. For example, a simple thermostatic switch may be implemented by means of a bimetallic strip to give a temperature dependent signal. Such a thermostatic switch can be set to switch on or off at a particular threshold temperature. More sophisticated and complex arrangements can be contemplated by use of other circuit elements to create other status indicators. For example, temperature status could be monitored more accurately by means of thermocouple junctions or thermistors to provide an analog electronic signal proportional to the temperature. Such circuit features could be integrated into the module using thin or thick film technology, e.g. pad or silk-screen printing of inks with a positive temperature coefficient (PTC) of resistance. Such PTC inks are known to the person skilled in the art. Such circuit elements may also be applied as labels. Other circuit elements may be used to provide other analog signals proportional to other physical properties of interest. For example, a light sensitive element such as a light dependent resistor, photodiode or phototransistor may be used to confirm that a module has been opened or a peel-able seal has been removed. Sensor readings, particularly environmental-related (such as temperature, humidity, light exposure, etc.) may be stored in the memory 400, particularly if the sensor readings are taken during storage and transportation of the modules 12. A timer may be also utilized to provide time stamps for the sensor readings. This allows for environmental data to be collected to determine if the related drug was exposed to hazardous conditions. Power may be provided in any known manner to allow for such sensor readings, timing, and data storage, prior to use of the modules 12. Power may be provided by on-board source(s), such as batteries, and/or by external sources, such as exposure to radio-frequency electromagnetic fields (with corresponding conversion hardware on the module). Upon assembly, the environmental data may be read out to evaluate stability of the drugs.

A disadvantage of using analog signals is that they need to be conditioned to interface with digital electronic circuits, which creates additional circuit complexity. This may require the integration of analog-digital converter (ADC) integrated circuits into the pump housing. In simple cases, if it is only required to threshold a signal (that is provide a logic high or low value depending on whether the signal is greater than or less than a threshold set-point) then this may be achieved simply using a comparator integrated circuit.

It is noted that control of the controller housing is discussed in the context of a CPU. As will be appreciated by those skilled in the art, the system may rely on logic which may be implemented in combinational and sequential logic circuits with some form of memory without the need for a stored program (software) running on a microprocessor. That is, the system logic may be hard-wired by design, which reduces the risk of logical errors inherent in software design and avoids the need for software validation, such as through the use of logic gates and the like.

Figure 21:
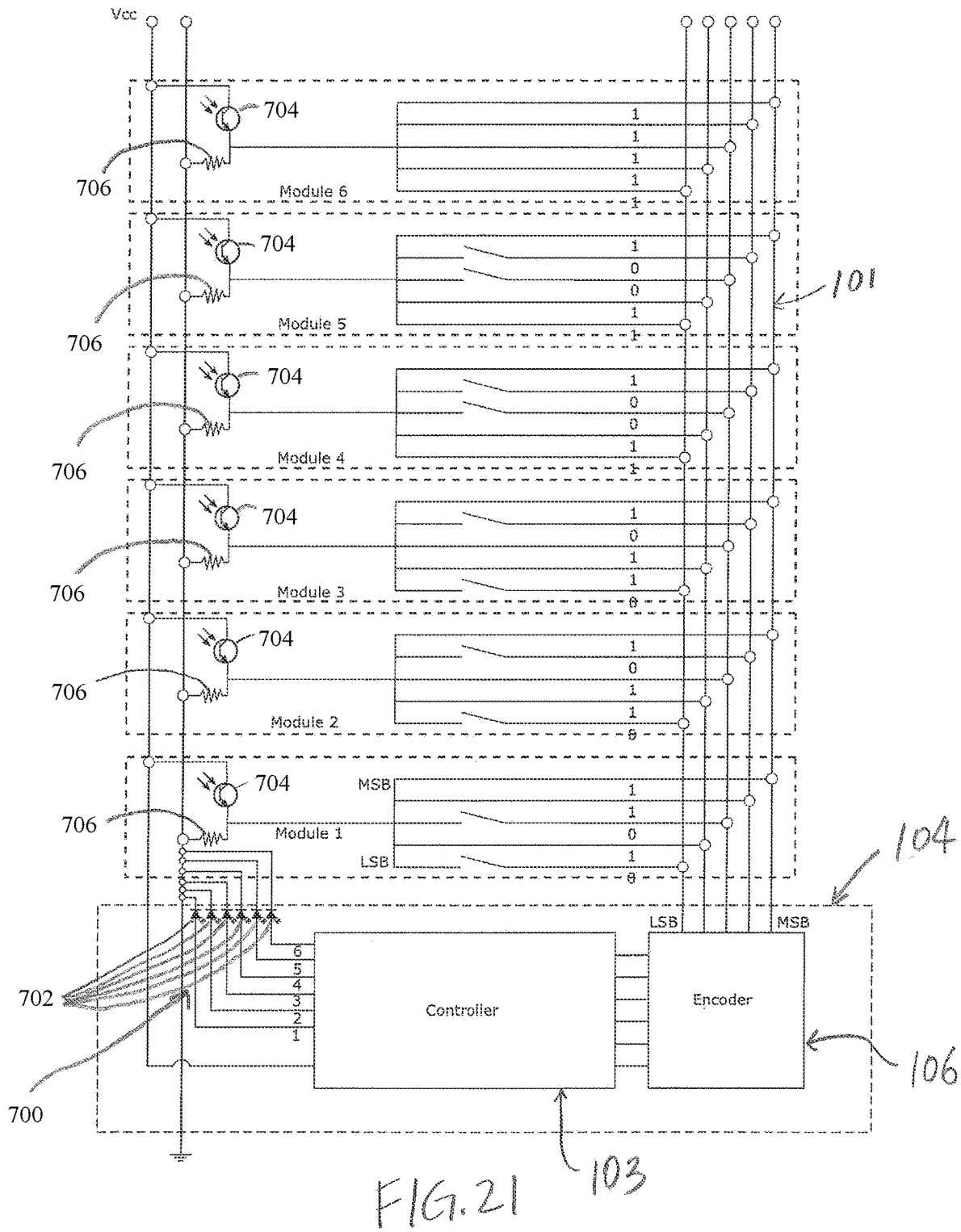
FIGS. 21-22 show use of an opto-electronic addressing system in place of the address bus.
Figure 22:
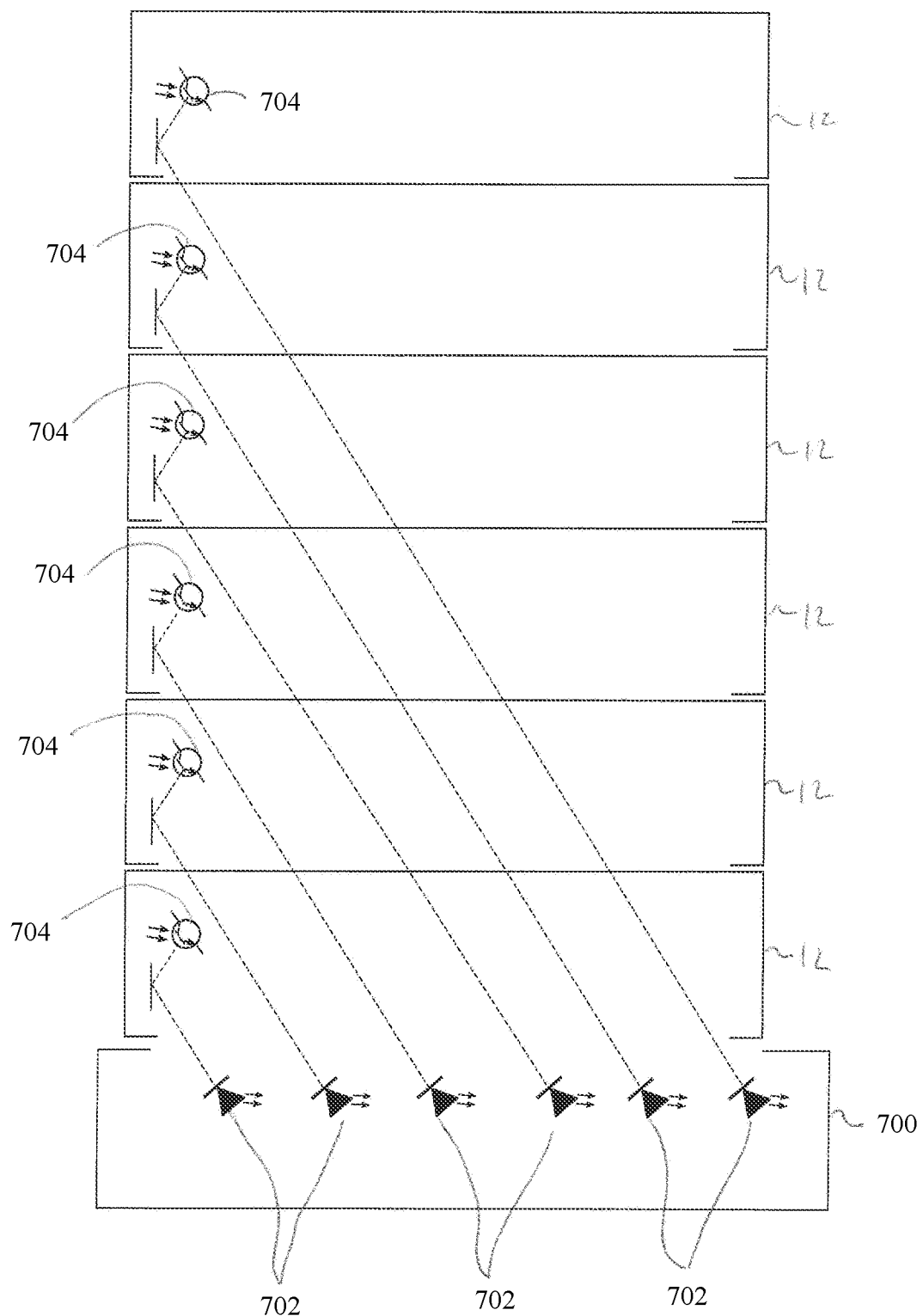

In an alternative embodiment, as shown in FIGS. 21-22, the address bus 102 may be replaced by an opto-electronic addressing system 700 comprising one or more light sources 702 which are preferably light-emitting diodes (LEDs) or diode lasers housed in the controller housing 104.

The controller 103 is provided with connections to a power and ground conductor. The modules 12 may be connected in series to the power and ground conductors. Each module 12 comprises a reflecting surface such as a mirror in its interior and a light sensitive element such as a phototransistor or photodarlington device 704 connected in series with a resistor 206 across the power and ground conductors in a common collector voltage divider circuit, the output of which connects to the switch array that encodes the binary number representative of the module type. The resistance of the resistor 706 is selected so that the common collector circuit is fully saturated so that the phototransistor or photodarlington (photo-sensor) 704 acts as an optical switch. With this configuration, when illuminated from the controller housing 104 by the light source 702, a potential equal to the power line voltage Vcc is applied across the switch array and the binary encoding for the addressed module appears on the data bus 101 at the input lines to the encoder 106.

Now by arranging for the controller 103 to illuminate the photo-sensors 704 in sequence by the sequential switched illumination of a plurality of light sources 702, as shown schematically in FIG. 22, the drug modules 12 can be addressed in sequence and their encodings interrogated.

In embodiments, instead of multiple light sources 702, one light source may be used in conjunction with optical and/or mechanical means for directing the beam to each photo-sensor 204 in turn.

An advantage of this system is that it involves no moving parts or mechanical bus connections in the modules 12 as it takes advantage of the ability for light to be transmitted without need for a physical transmission medium.

The system 700 requires a clear transmission path for the light beam and to this end narrow windows or slits may be provided in the modules 12 to allow for the unobstructed passage of light through the module stack. Alternatively, transparent windows may be provided in the modules 12 in which case consideration of the effect of refraction on the path of the transmitted beam resulting from the change of medium must be made, including allowance for manufacturing tolerances in the window material.

It will be appreciated by the person skilled in the art that optical components including but not limited to optical waveguides ('light pipes'), lenses, prisms, mirrors, collimators, pin-holes may be implemented in the control unit and/or the modules to refract, steer, expand and focus the light from the LED or laser diode to facilitate the optical addressing of the requisite drug module. Additionally, screens and/or optical filters may be used to prevent unintended switching due to external sources of illumination. In addition, the light sources may be any type of solid state lighting, including LEDs, OLEDs (organic light emitting diodes), and PLEDs (polymeric light emitting diodes).

Due consideration must also be given to matching of the spectral sensitivity of the photo-sensor to the spectral emissions of the light source.

In one embodiment, any of the combinatorial drug delivery devices or systems disclosed herein is able to deliver two or more drugs for the benefit of the patient suffering from any of a wide range of diseases or conditions, e.g., cancer, autoimmune disorder, inflammatory disorder, cardiovascular disease or fibrotic disorder. In one embodiment, one or more of drug module 12 may contain a single drug. In one embodiment, one or more of drug module 12 may contain two or more co-formulated drugs. In one embodiment, one or more of drug module 12 may contain a drug in solid form (such as a tablet, capsule, powder, lyophilized, spray dried), which can be reconstituted with flow of a diluent therein to form a liquid drug.

In one embodiment, one or more of the drugs of any of the combinatorial drug delivery devices disclosed herein is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, any of the combinatorial drug delivery devices disclosed herein includes a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, any of the combinatorial drug delivery devices disclosed herein includes a LAG3 antagonist, e.g., relatlimab or MK-4280, and a PD-1 pathway inhibitor, e.g., nivolumab (OPDIVO) or pembrolizumab (KEYTRUDA). In one embodiment, any of the combinatorial drug delivery devices disclosed herein includes a LAG3 antagonist, e.g., relatlimab or MK-4280, and a CTLA-4 antagonist, e.g., ipilimumab (YERVOY). In one embodiment, any of the combinatorial drug delivery devices disclosed herein includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDO1 antagonist. In another embodiment, the IDO1 antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2''-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of any of the combinatorial drug delivery devices disclosed herein is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+T lymphocyte); CD28CAR/CD137CAR-expressing T lymphocyte; allogeneic CD4+ memory Th1-like T cells/microparticle-bound anti-CD3/anti-CD28; anti-CD19/CD28/CD3zeta CARgammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of any of the combinatorial drug delivery devices disclosed herein is an anti-CD73 antibody or antigen binding fragment thereof. In certain embodiments, the anti-CD73 antibody is MEDI9447.

In one embodiment, one or more of the drugs of any of the combinatorial drug delivery devices disclosed herein is a TLR9 agonist. In one embodiment, the TLR9 agonist is agatolimod sodium.

In one embodiment, one or more of the drugs of any of the combinatorial drug delivery devices disclosed herein is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of any of the combinatorial drug delivery devices disclosed herein is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of any of the combinatorial drug delivery devices disclosed herein is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of any of the combinatorial drug delivery devices disclosed herein is a SHP-1 antagonist.

In one embodiment, one or more of the drugs of any of the combinatorial drug delivery devices disclosed herein is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of any of the combinatorial drug delivery devices disclosed herein is an agonist of a TNF family member. In some embodiments, the agonist of the TNF family member is ATOR 1016, ABBV-621, or Adalimumab.

In one embodiment, one or more of the drugs of any of the combinatorial drug delivery devices disclosed herein is an Interleukin-2 (IL-2), such as aldesleukin. Preferably, the IL-2 or conjugated IL-2 (e.g., pegylated) has been modified to selectively activate T-effector cells over T-regulatory cells ("T-eff IL-2"), such as bempegaldesleukin. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA). In one embodiment, any of the combinatorial drug delivery devices disclosed herein includes a modified IL-2, such as bempegaldesleukin, which selectively activates T-effector cells over T-regulatory cells, and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a CTLA-4 antagonist, e.g., ipilimumab (YERVOY), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), a CTLA-4 antagonist, e.g., ipilimumab (YERVOY), and a LAG3 antagonist, e.g., relatlimab or MK-4280.

In one embodiment, one or more of the drugs of any of the combinatorial drug delivery devices disclosed herein is a CD160 (NK1) agonist. In certain embodiments, the CD160 (NK1) agonist is an anti-CD160 antibody or antigen binding fragment thereof. In one embodiment, the anti-CD160 antibody is BY55.

In one embodiment, the one or more of drug module 12 may contain a soluble CTLA-4 polypeptide, which can be useful for treating, for instance, T-cell mediated autoimmune disorders, such as rheumatoid arthritis, juvenile idiopathic arthritis, psoriatic arthritis, graft-versus-host disease, and transplant rejection. In one embodiment, the soluble CTLA-4 polypeptide is abatacept (ORENCIA), belatacept (NULOJIX), RG2077, or RG-1046. In certain embodiments, one or more drug modules 12 of a combinatorial drug delivery device as described herein include a soluble CTLA-4 polypeptide, e.g., abatacept (ORENCIA) and a Bruton's tyrosine kinase inhibitor, e.g., branebrutinib. In certain embodiments, one or more drug modules 12 of a combinatorial drug delivery device as described herein include a soluble CTLA-4 polypeptide, e.g., abatacept (ORENCIA) and a tyrosine kinase-2 inhibitor, e.g., BMS-986165. In certain embodiments, one or more drug modules 12 of a combinatorial drug delivery device as described herein include a soluble CTLA-4 polypeptide, e.g., abatacept (ORENCIA) and an Interleukin-2 (IL-2) or "T-reg IL-2", which selectively activates T-regulatory cells as opposed to T-effector cells, e.g., BMS-986326 and NKTR-358.

What is claimed is:

1. A combinatorial drug delivery device comprising:
   a plurality of serially-connected drug modules, each of said drug modules accommodating a volume of liquid drug, said drug modules being serially-connected to define a flow path to deliver said liquid drug from all of said drug modules through an outlet;
   a valve and/or a pump for selectively controlling flow through said outlet;
   a controller for selectively controlling said valve and/or said pump;
   an address bus;
   a data bus;
   a data selector electrically coupled with said address bus; and,
   an encoder electrically coupled with said data bus,
   wherein, each of said drug modules includes a plurality of frangible electrical conductors,
   wherein, with said drug modules being serially-connected, said electrical conductors of each of said drug modules is electrically coupled to said address bus and to said data bus,
   wherein, for each of said drug modules, said electrical conductors being selectively broken to represent said liquid drug accommodated therein,
   wherein, said data selector being configured to select individually each of said electrical conductors within each of said drug modules,
   wherein, with application of electrical potential between said address bus and said data bus, across said electrical conductors, said encoder detecting which of said electrical conductors is broken and which is not broken, thereby providing a binary indication of the state of said respective electrical conductor,
   wherein, said controller collecting said binary indications of said electrical conductors to determine a data string corresponding to all of said drug modules in sequence, whereby said determined data string represents the liquid drug of each of said drug modules and the sequence of said drug modules,
   wherein, said controller having a memory with stored therein an expected data string, said controller configured to compare said determined data string with said expected data string, and,
   wherein, with a match between said determined data string and said expected data string, said controller configured to cause at least one of: said valve to open to permit flow through said outlet and/or said pump to open to drive flow through said outlet.

2. A combinatorial drug delivery device as in claim 1, wherein said memory of said controller is programmable to receive the expected data string.

3. A combinatorial drug delivery device as in claim 1, wherein each of said drug modules includes a portion of said address bus, said address bus being collectively formed by said drug modules being serially connected.

4. A combinatorial drug delivery device as in claim 3, wherein each of the drug modules further includes:
   a plurality of address line conductors to form respective said portion of said address bus;
   an axially shiftable position pin; and,
   a moveable contact arranged to be moveable into electrical connection, individually, with each of the address line conductors,
   wherein, the moveable contact is coupled to the position pin such that axially shifting the position pin causes the moveable contact to move between, and to selectively electrically connect with, the address line conductors.

5. A combinatorial drug delivery device as in claim 4, wherein, for each of said drug modules, said position pin has a length greater than a width of respective said drug module so that the position pin extends from respective said drug module in an initial state.

6. A combinatorial drug delivery device as in claim 1, wherein each of said drug modules includes a portion of said data bus, said data bus being collectively formed by said drug modules being serially connected.

7. A combinatorial drug delivery device as in claim 6, wherein, each of said drug modules includes a plurality of data transmission lines to form respective said portion of said data bus.

8. A combinatorial drug delivery device as in claim 7, wherein, for each of said drug modules, the quantity of said plurality of data transmission lines is equal to or greater than the quantity of said electrical conductors.

* * * * *